US008597280B2

(12) United States Patent
Cooper et al.

(10) Patent No.: US 8,597,280 B2
(45) Date of Patent: Dec. 3, 2013

(54) SURGICAL INSTRUMENT ACTUATOR

(75) Inventors: Thomas G. Cooper, Menlo Park, CA (US); Matthew R. Williams, Walnut Creek, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1436 days.

(21) Appl. No.: 11/762,172

(22) Filed: Jun. 13, 2007

(65) Prior Publication Data
US 2008/0058861 A1 Mar. 6, 2008

Related U.S. Application Data

(60) Provisional application No. 60/813,129, filed on Jun. 13, 2006.

(51) Int. Cl.
*A61B 17/00* (2006.01)

(52) U.S. Cl.
USPC ............................................. 606/1; 606/130

(58) Field of Classification Search
USPC ............................................. 128/898; 606/1
See application file for complete search history.

(56) References Cited

U.S. PATENT DOCUMENTS

| | | | | |
|---|---|---|---|---|
| 3,183,301 A * | 5/1965 | Kompanek, Jr. et al. | ..... | 174/108 |
| 3,815,061 A * | 6/1974 | Fujio | ............................... | 335/145 |
| 4,411,168 A * | 10/1983 | Yoshifuji | ...................... | 74/502.5 |
| 4,823,752 A * | 4/1989 | Uuskallio | ...................... | 123/400 |
| 4,907,553 A * | 3/1990 | Porter | ............................ | 123/400 |
| 5,700,275 A * | 12/1997 | Bell et al. | ....................... | 606/208 |
| 6,078,010 A * | 6/2000 | Funahashi et al. | .......... | 174/126.1 |
| 6,194,666 B1 * | 2/2001 | Hayashida et al. | ......... | 174/128.1 |
| 6,312,398 B1 * | 11/2001 | Cencer | ............................ | 601/40 |
| 6,347,561 B2 * | 2/2002 | Uneme et al. | ................. | 74/502.5 |
| 6,481,892 B1 * | 11/2002 | Agostini | ......................... | 384/43 |
| 6,945,979 B2 * | 9/2005 | Kortenbach et al. | ........... | 606/143 |
| 2002/0087049 A1 * | 7/2002 | Brock et al. | .................. | 600/114 |
| 2002/0087148 A1 * | 7/2002 | Brock et al. | ..................... | 606/1 |
| 2002/0177843 A1 * | 11/2002 | Anderson et al. | ............... | 606/1 |
| 2002/0198538 A1 * | 12/2002 | Kortenbach et al. | ........... | 606/139 |
| 2003/0036748 A1 * | 2/2003 | Cooper et al. | ..................... | 606/1 |
| 2006/0079884 A1 * | 4/2006 | Manzo et al. | ................... | 606/41 |
| 2006/0201130 A1 * | 9/2006 | Danitz | ............................ | 59/78.1 |
| 2007/0225754 A1 * | 9/2007 | Measamer et al. | ............ | 606/205 |
| 2008/0196533 A1 * | 8/2008 | Bergamasco et al. | ...... | 74/490.06 |

\* cited by examiner

*Primary Examiner* — Bill Thomson
*Assistant Examiner* — Jeffrey Lipitz

(57) ABSTRACT

A surgical instrument body has a proximal portion, a distal portion, and a joint between the proximal and distal instrument body portions. A drive element housing extends through the proximal and distal instrument body portions and through the joint. A force to actuate a component at the distal end of the instrument body is applied to the drive element. A second force in the opposite direction is applied to the drive element housing, and this second force is also applied to the component. The opposite direction forces stabilize the component so that when the distal component is actuated, the actuation does not significantly affect the joint position.

23 Claims, 23 Drawing Sheets

SURGICAL INSTRUMENT ACTUATOR

CROSS REFERENCE TO RELATED APPLICATIONS

This application claims the benefit of priority from U.S. Provisional Patent Application No. 60/813,129, filed 13 Jun. 2006, entitled "Minimum Net Force Actuation," the disclosure of which is incorporated by reference herein in its entirety.

This application is related to, and incorporates by reference in its entirety, concurrently filed U.S. patent application Ser. No. 11/762,185 entitled "Surgical Instrument Actuation System" by Thomas G. Cooper and Matthew R. Williams.

In addition, this application is related to the following concurrently filed United States Patent Applications, all of which are incorporated by reference:

U.S. patent application Ser. No. 11/762,217 entitled "Retraction of tissue for single port entry, robotically assisted medical procedures" by Mohr;

U.S. patent application Ser. No. 11/762,222 entitled "Bracing of bundled medical devices for single port entry, robotically assisted medical procedures" by Mohr et al.;

U.S. patent application Ser. No. 11/762,231 entitled "Extendable suction surface for bracing medical devices during robotically assisted medical procedures" by Schena;

U.S. patent application Ser. No. 11/762,236 entitled "Control system configured to compensate for non-ideal actuator-to-joint linkage characteristics in a medical robotic system" by Diolaiti et al.;

U.S. patent application Ser. No. 11/762,165 entitled "Minimally invasive surgical system" by Larkin et al.;

U.S. patent application Ser. No. 11/762,161 entitled "Minimally invasive surgical instrument advancement" by Larkin et al.;

U.S. patent application Ser. No. 11/762,158 entitled "Surgical instrument control and actuation" by Cooper et al.;

U.S. patent application Ser. No. 11/762,154 entitled "Surgical instrument with parallel motion mechanism" by Cooper;

U.S. patent application Ser. No. 11/762,149 entitled "Minimally invasive surgical apparatus with side exit instruments" by Larkin;

U.S. patent application Ser. No. 11/762,170 entitled "Minimally invasive surgical apparatus with side exit instruments" by Larkin;

U.S. patent application Ser. No. 11/762,143 entitled "Minimally invasive surgical instrument system" by Larkin;

U.S. patent application Ser. No. 11/762,135 entitled "Side looking minimally invasive surgery instrument assembly" by Cooper et al.;

U.S. patent application Ser. No. 11/762,132 entitled "Side looking minimally invasive surgery instrument assembly" by Cooper et al.;

U.S. patent application Ser. No. 11/762,127 entitled "Guide tube control of minimally invasive surgical instruments" by Larkin et al.;

U.S. patent application Ser. No. 11/762,123 entitled "Minimally invasive surgery guide tube" by Larkin et al.;

U.S. patent application Ser. No. 11/762,120 entitled "Minimally invasive surgery guide tube" by Larkin et al.;

U.S. patent application Ser. No. 11/762,118 entitled "Minimally invasive surgical retractor system" by Larkin;

U.S. patent application Ser. No. 11/762,114 entitled "Minimally invasive surgical illumination" by Schena et al.;

U.S. patent application Ser. No. 11/762,110 entitled "Retrograde instrument" by Duval et al.;

U.S. patent application Ser. No. 11/762,204 entitled "Retrograde instrument" by Duval et al.;

U.S. patent application Ser. No. 11/762,202 entitled "Preventing instrument/tissue collisions" by Larkin;

U.S. patent application Ser. No. 11/762,189 entitled "Minimally invasive surgery instrument assembly with reduced cross section" by Larkin et al.;

U.S. patent application Ser. No. 11/762,191 entitled "Minimally invasive surgical system" by Larkin et al.;

U.S. patent application Ser. No. 11/762,196 entitled "Minimally invasive surgical system" by Duval et al.; and U.S. patent application Ser. No. 11/762,200 entitled "Minimally invasive surgical system" by Diolaiti.

BACKGROUND

1. Field of Invention

The invention relates to surgical instruments.

2. Background Art

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas and cannula sleeves are passed through small (approximately ½-inch) incisions in the musculature of the patient's abdomen to provide entry ports through which laparoscopic surgical instruments can be passed in a sealed fashion.

The laparoscopic surgical instruments generally include a laparoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by an approximately 12-inch long extension tube, for example, so as to permit the operator to introduce the end effector to the surgical site and to control movement of the end effector relative to the surgical site from outside a patient's body.

In order to provide improved control of the working tools, it may be desirable to provide the instrument with one or more degrees of freedom at an intermediate location proximal to the end effector. For example, some instruments include a wrist assembly providing multiple degrees of freedom for positioning the end effector. Cables are used to actuate movement of the wrist assembly and the end effector. Because the cables controlling the end effector must first pass through the wrist assembly in order to reach the end effector, these cables may undesirably apply forces to the wrist assembly. In such situations, for example, a quick reduction in a force used to operate an end effector may cause the wrist mechanism to move, which is undesirable.

It is desirable to provide an instrument capable of transmitting forces to a distal object without undesirably applying forces to intermediate structures in the instrument.

SUMMARY

In accordance with aspects of the invention, a surgical instrument includes a body with a proximal portion, a distal portion, and at least one joint between the proximal and distal portions. A drive element housing extends through the proximal and distal instrument body portions and through the joint. A drive element extends through the drive element housing. A force applied to the drive element actuates a component coupled to the distal end of the instrument body. A force opposite to the force on the drive element is applied to the drive element housing, and the drive element housing transmits this force to the component. The counteraction stabilizes the distal end component so that actuation forces are acceptably minimized or eliminated at the joint. An example of a distal component is a surgical end effector. For instance, the drive element operates the end effector's jaws, and the drive element housing applies force against the clevis that holds the jaws.

Other features and aspects of the invention will become apparent from the following detailed description, taken in conjunction with the accompanying drawings which illustrate, by way of example, the features in accordance with embodiments of the invention. The summary is not intended to limit the scope of the invention, which is defined solely by the claims.

DETAILED DESCRIPTION

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
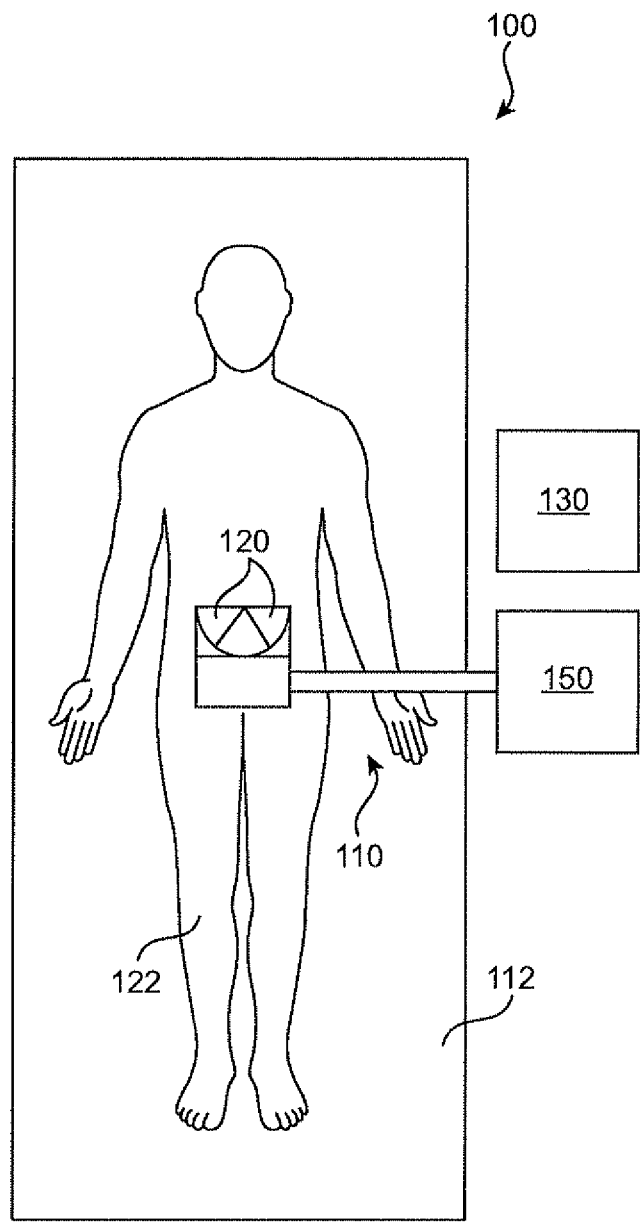
FIG. 1 is a simplified block diagram of a surgical system in accordance with embodiments of the present invention.

FIG. 1 is a simplified block diagram of a surgical system 100, in accordance with embodiments of the present invention. The system 100 includes a surgical assembly 110 mounted to or near an operating table 112 supporting a patient's body 122. The surgical assembly 110 enables the delivery of one or more surgical instruments 120 to a surgical site within the patient's body 122.

The term "instrument" is used herein to describe a device configured to be inserted into a patient's body and used to carry out surgical procedures. The instrument may comprise a single surgical tool, such as a needle driver, a cautery device, or a cutting tool, an imaging device (e.g., an endoscope or ultrasound probe), or a combined device that includes a combination of two or more various tools and imaging devices.

The system 100 further includes a vision system 130 that enables the operator to view the surgical site from outside the patient's body 122. The vision system 130 may comprise, e.g., a video monitor displaying images received by an optical device provided at a distal end of one of the surgical instruments 120. The optical device may comprise, e.g., a lens coupled to an optical fiber which carries the detected images to an imaging sensor (e.g., a CCD or CMOs sensor) outside of the patient's body 122. Alternatively, the imaging sensor may be provided at the distal end of the surgical instrument 120, and the signals produced by the sensor are transmitted along a lead or wirelessly for display on the monitor. An illustrative monitor is the stereoscopic display on the surgeon's cart in the da Vinci® Surgical System, manufactured by Intuitive Surgical, Inc., of Sunnyvale Calif.

A control system 150 is provided for controlling the insertion and articulation of the surgical assembly 110 and surgical instruments 120. This control may be effectuated in a variety of ways, depending on the degree of control desired, the size of the surgical assembly 110, and other factors. In some embodiments, the control system 150 may include one or more manually operated input devices, such as a joystick, exoskeletal glove, or the like. These input devices control servo motors which, in turn, control the articulation of the surgical assembly 110. The forces generated by the servo motors are transferred via drivetrain mechanisms, which transmit the forces from the servo motors generated outside the patient's body 122 through an intermediate portion of the elongate surgical assembly 110 to a portion of the surgical assembly 110 inside the patient's body 122 distal from the servo motor. The drivetrain mechanism may comprise, e.g., cables in tension, or rods or tubes in compression or under torsion. Persons familiar with telemanipulative surgery will know of systems such as the da Vinci® Surgical System and the Zeus® system originally manufactured by Computer Motion, Inc. and various illustrative components of such systems.

Figure 2A:
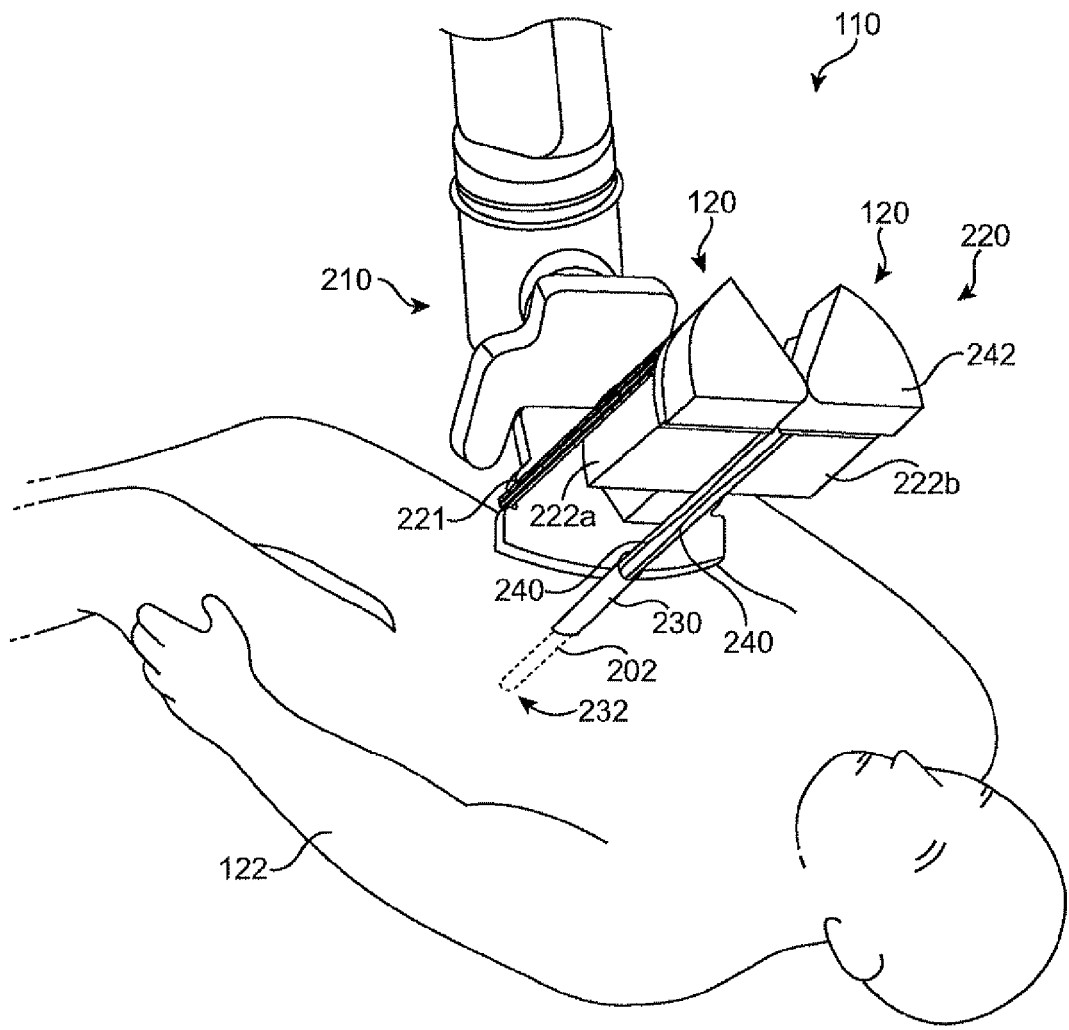
FIGS. 2A and 2B are upper and lower perspective views, respectively, of a surgical assembly inserted through a port in a patient's abdomen.
Figure 2B:
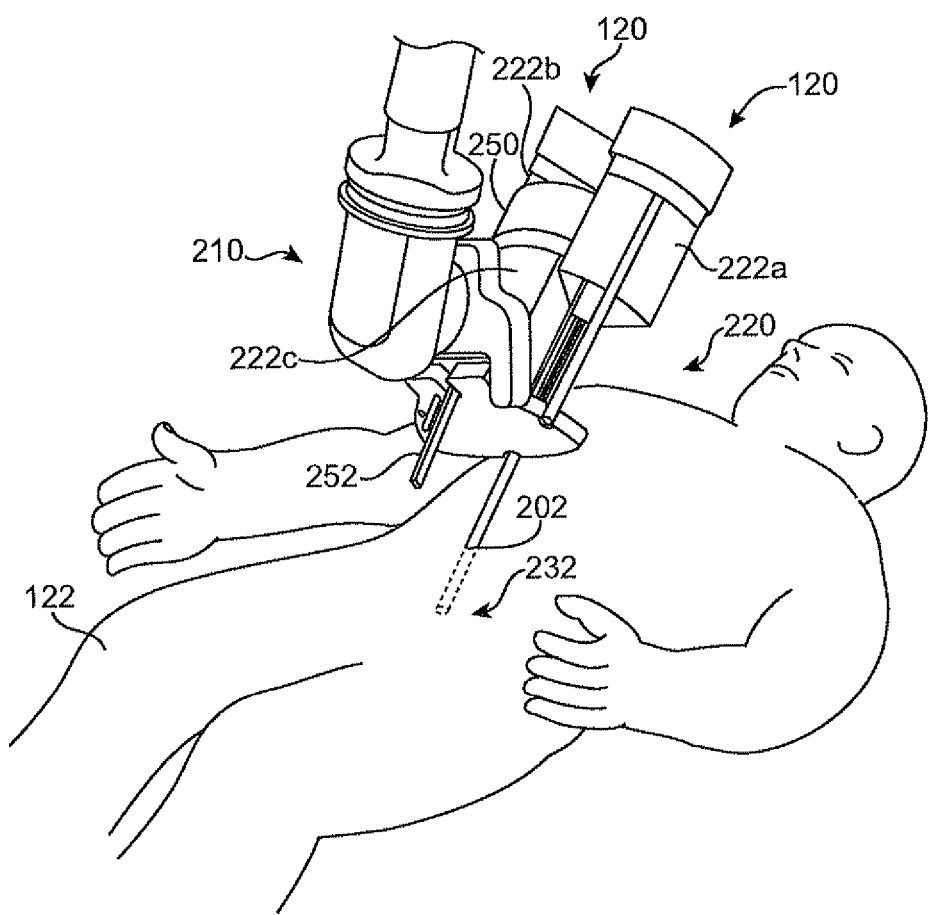

FIGS. 2A and 2B are upper and lower perspective views, respectively, of a surgical assembly 110 inserted through, e.g., a single port 202 in a patient's abdomen (the entry guide cannula is not shown). The surgical assembly 110 comprises an entry guide manipulator 210 and an instrument manipulator 220. An entry guide 230 is mounted onto the entry guide manipulator 210, which includes a robotic positioning system for positioning the distal end 232 of the entry guide 230 at the desired target surgical site. The robotic positioning system may be provided in a variety of forms, such as, e.g., a serial link arm having multiple degrees of freedom (e.g., six degrees of freedom) or a remote center arm which is positioned by a setup joint mounted onto a base. Alternatively, the entry guide manipulator 210 may be manually maneuvered so as to position the entry guide 230 in the desired location. In some telesurgical embodiments, the input devices that control the manipulator(s) may be provided at a location remote from the patient (outside the room in which the patient is placed). The input signals from the input devices are then transmitted to the control system 150, which, in turn, manipulates the manipulators 210, 220 in response to those signals. The instrument manipulator 220 is coupled to the entry guide manipulator 210 such that the instrument manipulator 220 moves in conjunction with the entry guide 230.

Figure 3A:
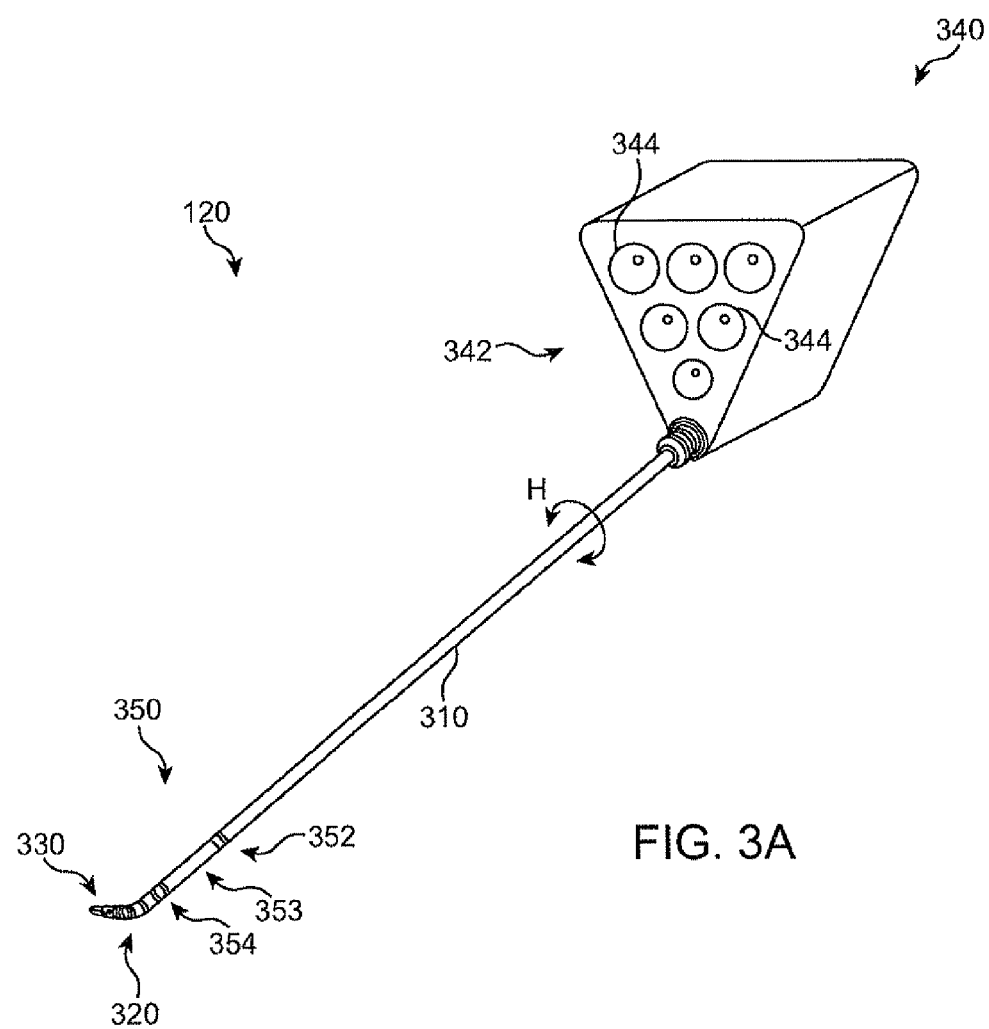
FIG. 3A is a perspective view of a surgical instrument.
Figure 3B:
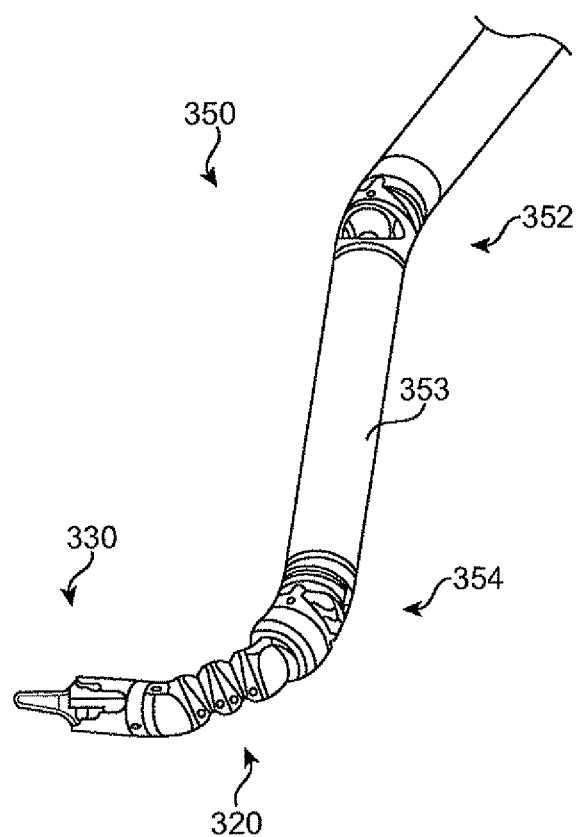
FIG. 3B is a perspective view of the distal portion of the surgical instrument shown in FIG. 3A.

FIG. 3A is a perspective view of an illustrative embodiment of the surgical instrument 120, comprising an elongate body portion tube 310, a distal portion 350, and a proximal control mechanism 340. FIG. 3B is a perspective view of the distal portion 350 of the surgical instrument 120 in more detail. In this embodiment, the distal portion 350 comprises a first hinge mechanism 352, a rigid forearm tube 353, a second hinge mechanism 354, a wrist assembly 320, and an end effector 330. The control mechanism 340 includes a drive interface 342, which mates with an instrument interface of a corresponding instrument manipulator 220. A disposable interface mechanism may be inserted between drive interface 342 and the instrument manipulator's instrument interface. The disposable interface can be used to facilitate sterile draping. The drive interface 342 comprises a plurality of driven elements 344, which are variously coupled via one or more drive train assemblies through the control mechanism 340 and body portion 310 to hinge assemblies 353, 354, wrist assembly 320, and end effector 330 provided at the distal end of the instrument 120. The drive trains are not necessarily separate, and in one embodiment are coupled so that moving pairs of driven elements 344 moves a distal end component. In some embodiments, the body portion 310 is rotatably coupled to the control mechanism 340 to enable rotational displacement of the body portion 310 relative to the control mechanism 340, as indicated by arrows H. In such embodiments, at least one drive element 344 is associated with rotating body 310.

Figure 4A:
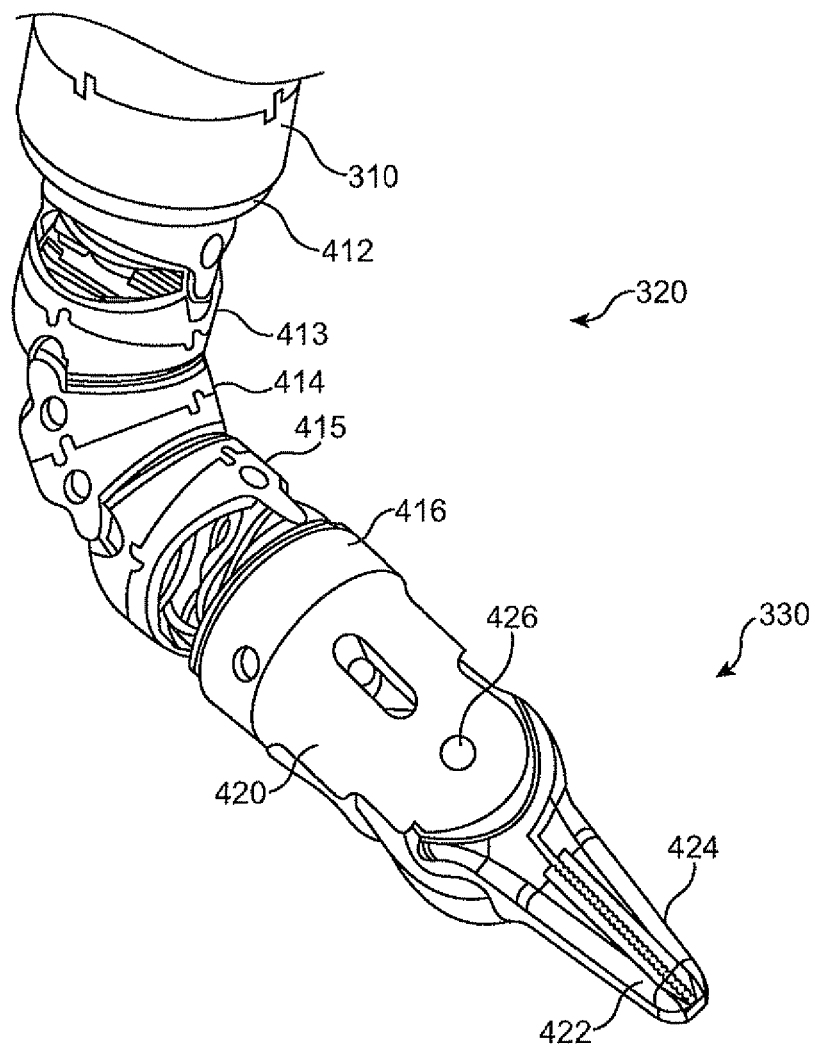
FIGS. 4A and 4B are perspective views of the wrist and end effector of the surgical instrument of FIGS. 3A and 3B.
Figure 4B:
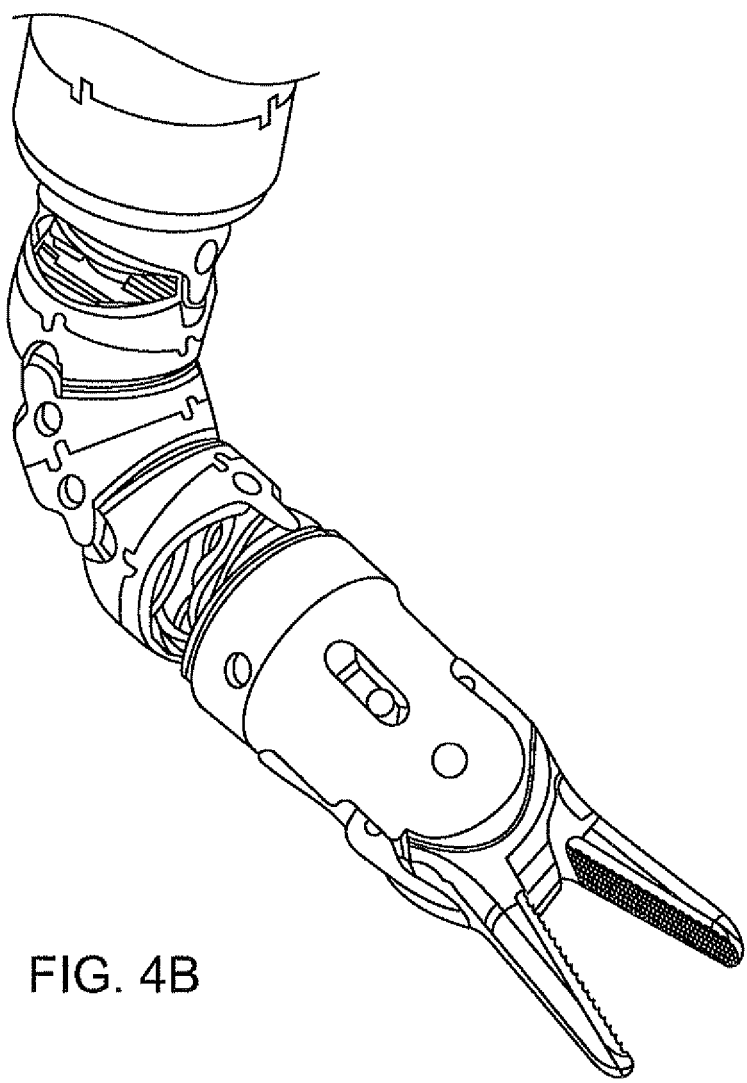

FIGS. 4A and 4B are perspective views of the wrist assembly 320 and end effector 330 of the surgical instrument 120, with the end effector 330 in closed and open positions, respectively. A similar device is described in U.S. Pat. No. 6,817,974, issued Nov. 16, 2004, to Thomas G. Cooper, et al., the disclosure of which is incorporated by reference herein in its entirety. The wrist assembly 320 includes a first or proximal link 412, which functions as an adaptor that couples the wrist assembly to the distal end of the body portion 310, a second link 413, a third or middle link 414, a fourth link 415, and a fifth or distal link 416, which functions to couple the wrist assembly to the end effector. End effector 330 includes gripper clevis 420, which is coupled to distal link 416. Clevis 420 supports a pair of working members or jaws 422, 424. To facilitate jaw movement, the jaws 422, 424 are rotatably supported by the gripper clevis 420 to rotate around pivot pin 426. The jaws 422, 424 shown are merely illustrative, and in other embodiments other types of end effectors, such as scissors, may be used.

Drive elements (not shown, but similar to those described in U.S. Pat. No. 6,817,974) are used to transmit actuating forces from control mechanism 340 to the components at instrument 120's distal end. Drive elements may be made in whole or in part of "filars" or filar-like components (the term "filars" as used herein should be broadly construed to include cables, hypotubes, single wires or rods (essentially similar at small diameters), various cable/wire/hypotube combinations, and any other long, thin component). A first set of drive elements actuates the wrist mechanism. Wrist actuation cables extend through adjacent sets of apertures in the links in the wrist mechanism. The free ends of the cables extend proximally through distal portion 350 and body portion 310 and are coupled at control mechanism 340 to driven elements 344. In addition, a second set of one or more drive elements are used to move the end effector 330. Each of the links 412-416 in the wrist has a hole in its center, and together the holes in the links define a central lumen in the wrist assembly. The second set of drive elements pass from the end effector working member(s) (e.g., gripping jaws), through the central lumen formed by the annular links 412-416, through distal portion 350, and through the body portion 310 to the control mechanism 340, where these cables are manipulated based upon the inputs to the driven elements 344.

In accordance with embodiments of the present invention, one or more drive elements (e.g., actuation wire, cable, hypotube) pass through an intermediate joint region (e.g., wrist assembly 320, hinge mechanisms 352,354) to extend to and move a movable mechanism (e.g., end effector 330) that is distal of the intermediate joint region. These drive elements are contained in a drive element housing that also extends through the intermediate joint region. A force is applied to the drive element housing that is opposite to the actuating force on the drive elements. The opposite drive element and drive element housing forces combine so as to reduce the amount of force applied to the intermediate joint region when actuating the articulating mechanism.

Referring again to FIG. 3A, drive forces are received by the driven elements 344 in control mechanism 340 at the proximal end of the instrument 120. These forces are transmitted by actuator assemblies inside control mechanism 340 to the movable, actuatable parts (e.g., instrument body, joints, wrist, end effector) of the instrument 120. Various mechanisms can be used, as described in more detail below.

Proximal Portion of the Surgical Instrument

Figure 5:
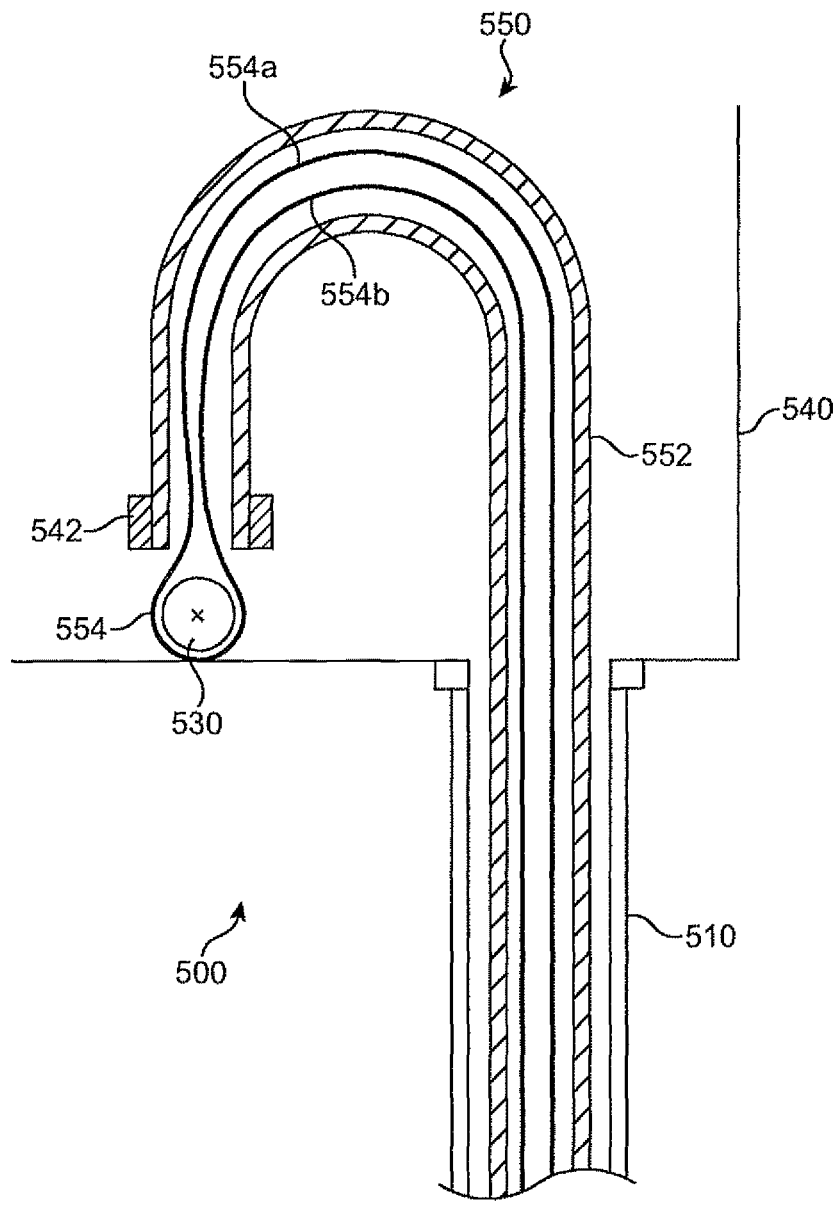
FIG. 5 is a cross-sectional view of a portion of a surgical instrument.

FIG. 5 is a diagrammatic cross-sectional view of a portion of surgical instrument 500 and a portion of its control mechanism 540. As shown in this illustrative embodiment, an actuator assembly 550 for a moveable distal component of instrument 500 includes a cable 554 (a drive element). Two portions 554a,554b (drive elements) of cable 554 run through a housing 552 (the drive element housing). The distal ends of cables 554a,554b are attached to and move the end effector (not shown). The actuator assembly 550 also includes a capstan 530, which is coupled to (e.g., with gears) and is driven by one of the driven elements 344 (FIG. 3A). As depicted in FIG. 5, cable 554 is looped around capstan 530. Therefore, cable portions 554a and 554b move in opposite directions within housing 552 as capstan 530 rotates. In this illustrative embodiment, only a tensile actuating force is applied by one of the cables 554a,554b.

As shown in FIG. 5, the proximal end of housing 552 is anchored to the chassis of the control mechanism 540 with anchor 542. The distal end (not shown) of housing 552 rests against a distal component being actuated by cables 554a, 554b. Although not shown in FIG. 5 for clarity, the cable ends 554a, 554b are in contact with the inner wall of the curve in housing 552. When a tensile force is applied to one of the ends 554a,554b by the capstan 530, the end 554a,554b applies a force to the inner surface of the curve in housing 552. Therefore anchor 542 and the distal component being actuated apply opposing forces to the housing 552. Thus, the forces applied by the cable 554 onto the inner wall of the housing 552 are offset by the forces being applied to the housing 552 by the anchor 542 and the distal component. As a result any intermediate structures through which the actuator assembly 550 passes are not affected by the forces being applied to the cable 554. Aspects of the actuator assembly's drive element and drive element housing, which extend through the instrument's movable intermediate structures, are discussed in more detail below.

In other embodiments, the two ends 554a,554b may be carried in separate housings to the end effector. In yet other embodiments, two separate cables may be used to actuate movement of the end effector, rather than the two ends of a single cable.

It can be seen that there is a "bend angle" associated with the actuator assembly. As shown in FIG. 5, for example, the bend angle is the total amount of bending that the drive element experiences between the capstan and the distal component being actuated. The bend angle may vary in other embodiments, depending on component placement.

Figure 6:
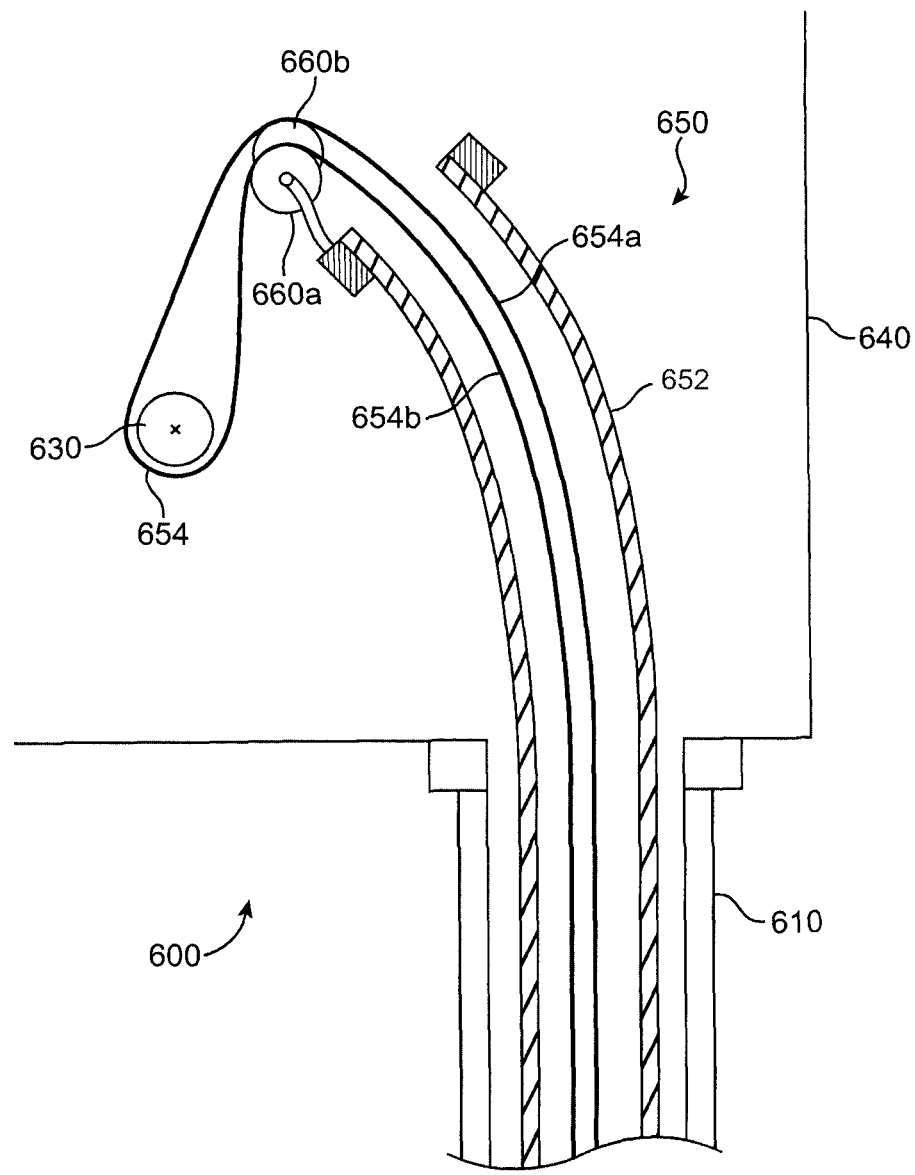
FIG. 6 is a cross-sectional view of a portion of another surgical instrument.

FIG. 6 is a cross-sectional view of a portion of a surgical instrument 600, in accordance with another embodiment. Similar to instrument 500 shown in FIG. 5, the actuator assembly 650 includes a cable 654 (drive element) contained in a housing 652 (drive element housing). Actuator assembly 650 also includes a capstan 630, which is coupled to one of the driven elements 344 in control mechanism 640. Cable 654 wraps around capstan 630. In this embodiment, the two ends 654a,654b of cable 654 engage a pair of idler pulleys 660a, 660b, which are anchored to the proximal end of drive element housing 652. Each cable end 654a,654b runs over its associated idler pulley 660a,660b before it enters drive element housing 652.

In this embodiment, the drive element housing 652 has a slight bend at its proximal end. The remainder of the bend angle for the cables 654a,654b is provided by the idler pulleys 660a,660b, thereby providing a total bend angle of greater than 90 degrees. In the embodiment shown in FIG. 5, the cable 554 experiences some degree of friction with the housing 552 because the actuator assembly 550 is bent 180 degrees. The use of the pulleys (e.g., idler pulleys 660a,660b in FIG. 6) can reduce the friction experienced by the cable. By providing a slight bend in the housing 652 before the cable 654 engages the pulleys 660a,660b, a single pair of pulleys 660a,660b may be used. Nevertheless, if the housing 652 is straight, a pair of pulleys may be used to establish a bend angle of 90 degrees. It can be seen that as a tensile force is applied to one of the actuator cables 654a,654b, its associated idler pulley 660a,660b applies an approximately opposite force on the proximal end of drive element housing 652. The force on drive element housing 552 is transmitted to the component being actuated at the distal end of the drive element housing. As described before, the opposite drive element and drive element housing forces on the distal component being actuated, while not equal, may effectively reduce or eliminate interfering forces on any intermediate joints through which the forces are transmitted.

Figure 7A:
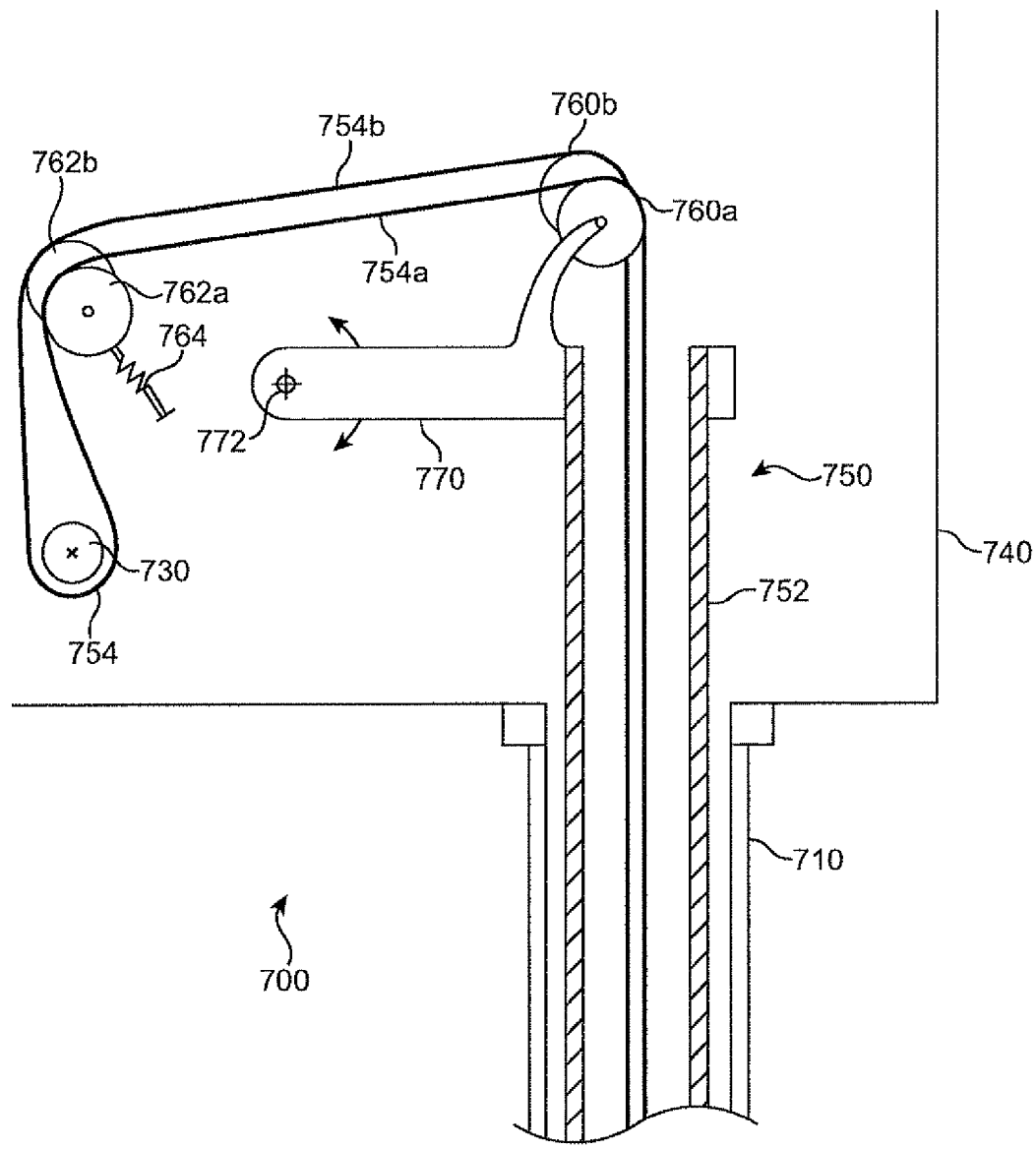
FIGS. 7A and 7B are cross-sectional views of portions of surgical instruments.

FIG. 7A is a cross-sectional view of a portion of another surgical instrument 700. Similar to instrument 500 shown in FIG. 5, the actuator assembly 750 includes a cable 754, which partially runs in a housing 752, and a capstan 730, which is rotatably coupled to the chassis of the control mechanism 740 and is driven by one of the driven elements of the drive interface of the control mechanism 740. In this embodiment actuator assembly 750 includes a support link 770, which has a proximal end rotatably coupled at first pivot point 772 to the chassis for the control mechanism 740. The distal end of the rotatable support link 770 supports the proximal end of the housing 752 such that the housing 752 is free to translate axially (i.e., along the longitudinal axis) through the elongate body portion 710.

The support link 770 further supports a first pair of idler pulleys 760a,760b, which receive the two ends 754a,754b of the cable 754. The two ends 754a,754b of the cable 754 form a wrap angle of at least 90 degrees around the pulleys 760a, 760b, respectively. In this embodiment, the wrap angle is exactly 90 degrees. A cable support structure applies a small amount of force to the cable 754 to maintain tension in the cable 754 between the first pair of pulleys 760a,760b and the capstan 730. In this embodiment, the cable support structure comprises a second pair of pulleys 762a,762b, which are resiliently mounted to the chassis for the control mechanism 740 (e.g., using a spring 764). The cable support structure may be provided with a maximum compliance such that when the cable 754 is under tension, the cable support structure will compress to the maximum compliance and then stop. Therefore, the compression compliance is minimized. However, when the cable 754 is not being used to apply a tensile force, the cable support structure will maintain some minimal tension in order to prevent the cable 754 from slipping off the pulleys 760a-760b.

Figure 7B:
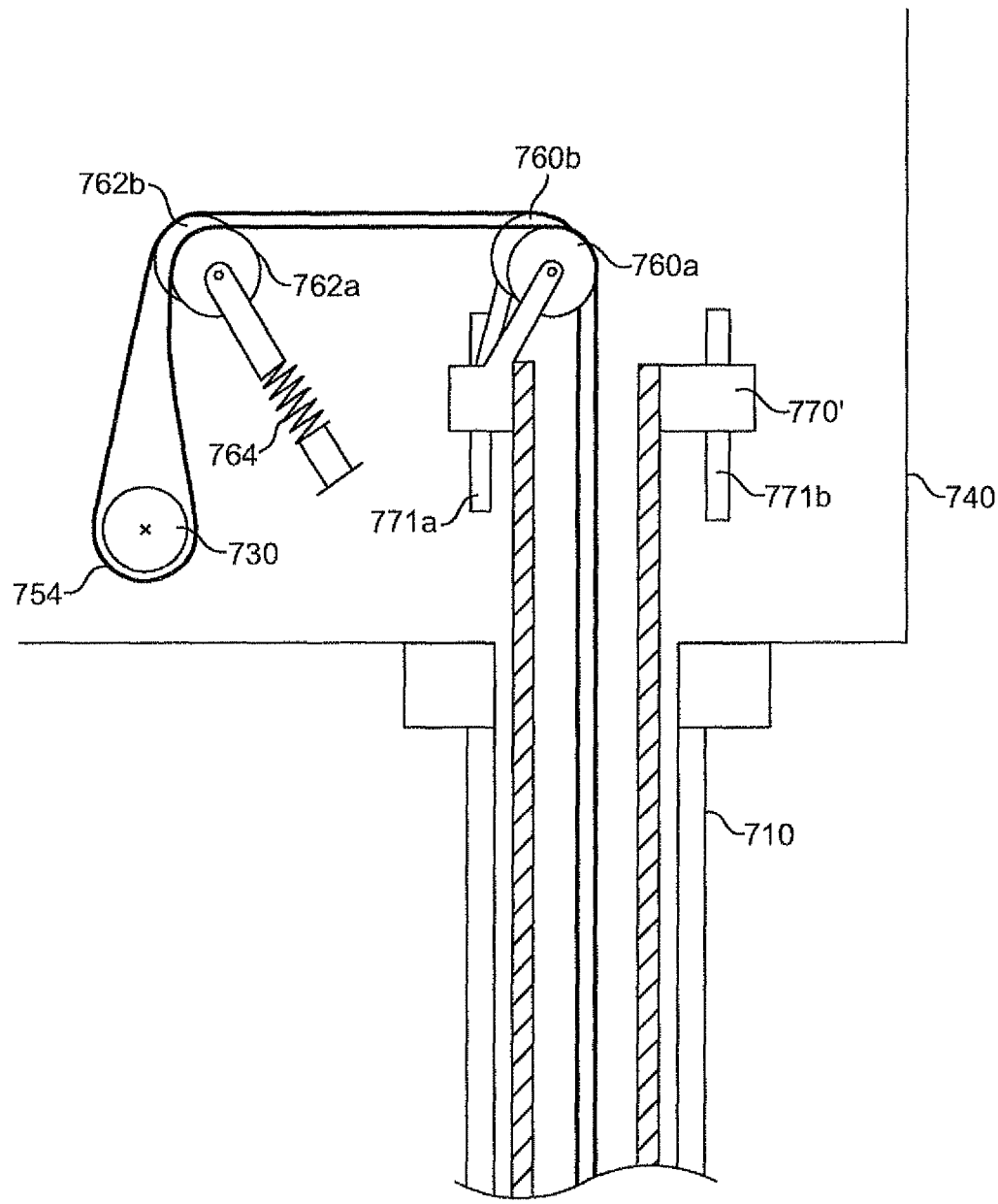

Because the support link 770 is movably mounted within the control mechanism 740 and supports both the cable housing 752 and the cable 754, the support link 770 applies a compressive force to the cable housing 752 substantially equal to the tensile force being applied by the idler pulleys 760a, 760b on the cable 754. This application to the housing of an equal and opposite force as the force applied to the cable results in a substantially zero net force on the intermediate structures between the input force and the structure being actuated (e.g., no net force applied to the wrist assembly 320 when the end effector 330 is being actuated). Thus, very high forces can be transmitted to the actuated structure without causing unwanted articulation of the intermediate structures. In other embodiments, the support link may be used to apply a force onto the housing that is less than the force applied to the cable. Although this will not ensure a substantially zero net force, as in FIG. 7, this counterforce may be sufficient to prevent the unwanted articulation of the intermediate structures.

In this embodiment, the support link 770 is rotatably mounted to the chassis of control mechanism 740. However, in other embodiments, other mechanisms permitting relative movement between the support link 770 and the input force (e.g., capstan 730) may be used, such as, e.g., rails, linear bearings, flexural supports, etc. One embodiment is illustrated in FIG. 713. Here, the support link 770' is slidably mounted to a pair of rails 771a,771b rather than being rotatably mounted to the first pivot point 772.

The drive element or elements need not be cables under tensile force. In accordance with other embodiments of the present invention, a single drive element that transmits both compressive and tensile forces may be used. For example, a rigid shaft, solid or hollow, of various cross-sectional shapes or a wire may be used. Or, a cable may be placed within a close fitting housing that prevents buckling so that the cable can transmit a compressive force. Likewise, the drive element housing need not completely surround the drive element. Thus "housing" is merely an illustrative term and encompasses other components (e.g., a shaft) that perform a similar function of transmitting a force, opposite to the direction of an actuating force for a distal instrument component, to the distal instrument component.

Figure 8:
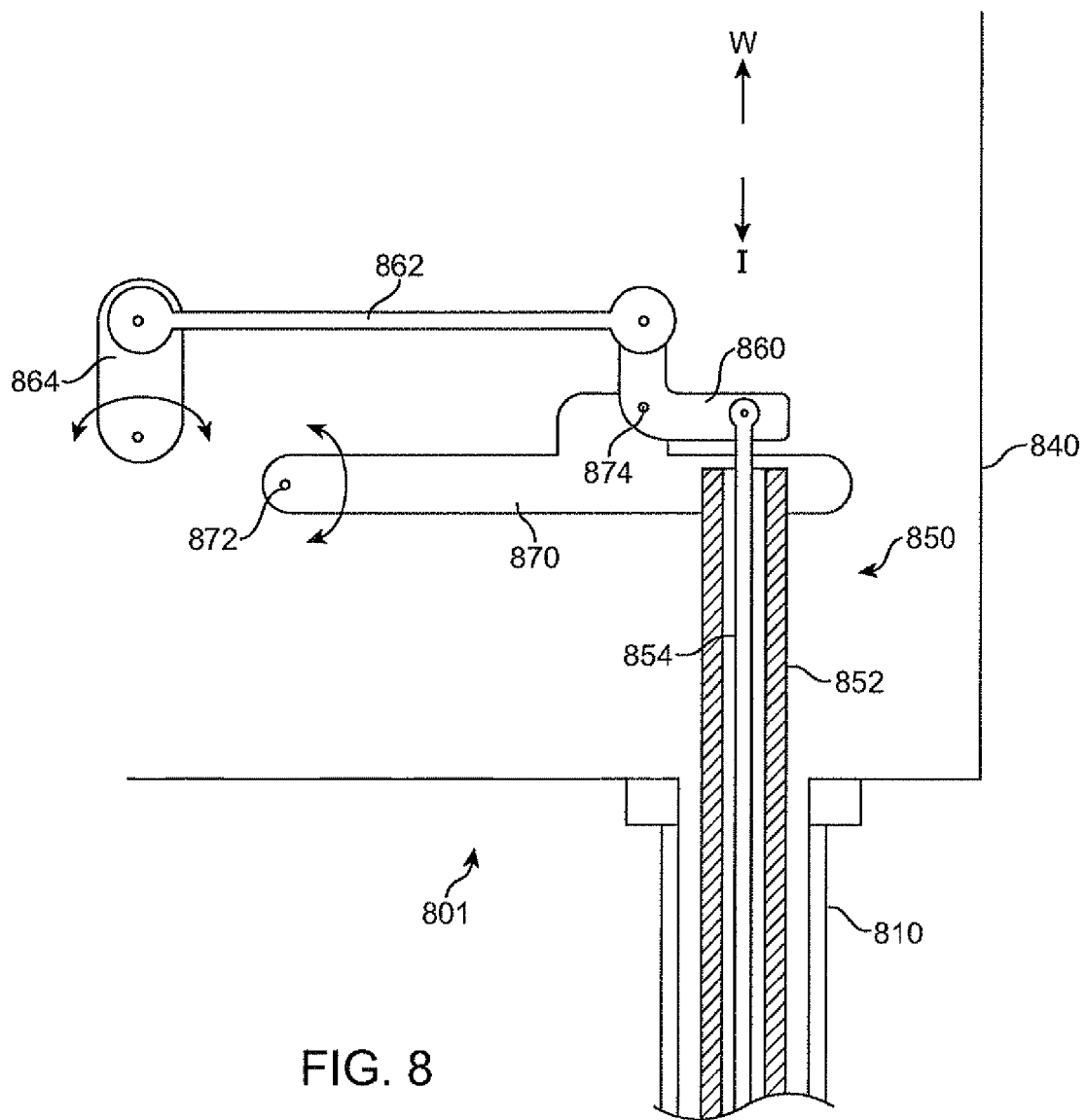
FIG. 8 is a cross-sectional view of a portion of another surgical instrument.

FIG. 8 is a cross-sectional view of a portion of a surgical instrument 800 having an illustrative single drive element 854 transmitting both compressive and tensile forces. In this embodiment, the drive element 854 is a rod or a cable contained in a close-fitting drive element housing 852 that prevents the cable from buckling. A support link 870 has a proximal end rotatably coupled to the chassis for the control mechanism 840 at first pivot point 872 and a distal end supporting the proximal end of the housing 852, such that the housing 852 is free to translate axially through the elongate instrument body portion 810.

As described above with reference to capstans, the rotational input force applied to the driven element 344 (FIG. 3) of the control mechanism 840 is transmitted to an input link 864. A distal end of the input link 864 is rotatably coupled to a proximal end of a coupling link 862. The distal end of the coupling link 862 is rotatably coupled to a proximal end of an L-shaped class 1 lever 860. The distal end of the lever 860 is rotatably coupled to the drive element 854 and an intermediate portion of the lever 860 is rotatably coupled to a second pivot point 874 (the fulcrum) on the support link 870. The force applied by lever 860 at its fulcrum 874 causes lever 870 to act as a class 3 lever with a fulcrum at 872.

Rotational movement of the link 864 due to the input force is transferred by the coupling link 862 to cause rotation of the lever 860 about the second pivot point 874. This rotation causes the drive element 854 to translate axially through the housing 852. In addition, the second pivot point 874 applies a roughly equal and opposite force on the support link 870 as is applied to the drive element 854. For example, if the input link 864 is rotated in the clockwise direction, this causes the lever 860 to rotate about the second pivot point 874 and apply a compressive force onto the drive element 854 in the insertion (towards the distal end) direction, I. In addition, the second pivot point 874 causes the support link 870 to rotate in a counterclockwise direction, which applies a tensile force on the housing 852 in the withdrawal (towards the proximal end) direction, W. As a result of the simultaneous compressive and tensile forces, the net force on the intermediate structures approaches zero. It may be desirable for the second pivot point 874 to be a close as possible to the drive element 854 such that this distance is small relative to the distance between the second pivot point 874 and the first pivot point 872. This positioning will ensure that the forces on the support link 870 are a close as possible to the opposite forces applied to the drive element 854. It can be seen that if link 864 is pivoted in the opposite direction, actuator assembly 850 similarly causes a tensile force on drive element 854 and a compressive force on drive element housing 852.

Figure 9A:
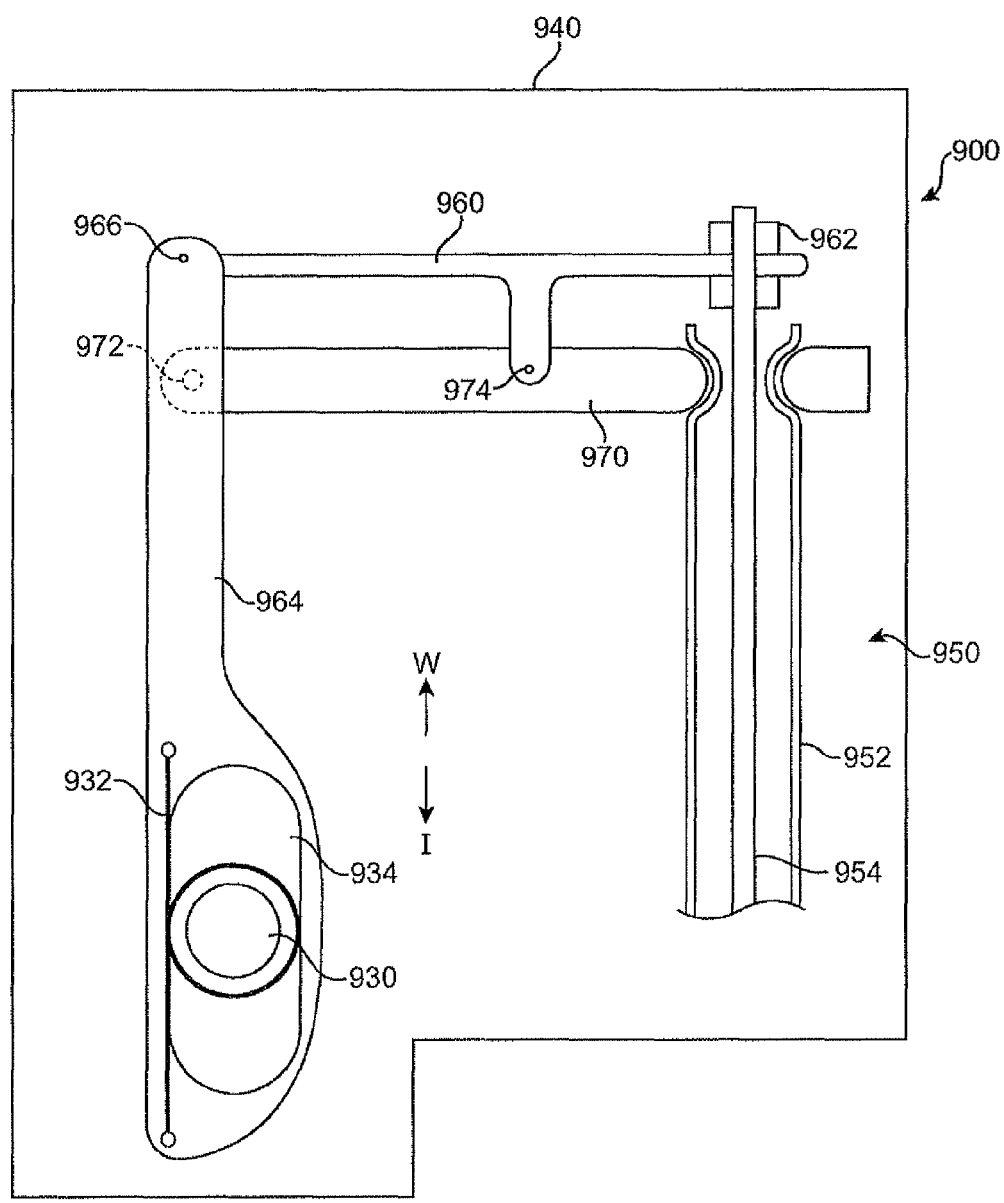
FIGS. 9A and 9B are cross-sectional views of portions of other surgical instruments.

FIG. 9A is a cross-sectional view of a portion of a surgical instrument 900 having a single drive element 954 that transmits both compressive and tensile actuating forces to a movable distal end component, in accordance with another embodiment of the present invention. Drive element 954 is contained in a drive element housing 952 that extends through the instrument body (not shown) and an intermediate moveable structure (not shown). A support link 970 has a proximal end rotatably coupled to the chassis for the control mechanism 940 at first pivot point 972 and a distal end that supports the proximal end of housing 952. As shown in FIG. 9A, the connection between support link 970 and drive element housing 952 is such that the housing 952 rotatably supports (e.g., with a bearing) the proximal end of the support link 970. The illustrative figure shows that the proximal end of drive element housing is slightly concave and fits within a mating convex-edged hole in link 970. This connection allows drive element housing 952 to rotate around its longitudinal axis but not move longitudinally with reference to link 970. Thus link 970 can apply a tensile or compressive force to drive element housing 952 while drive element housing 952 rotates within link 970.

In this embodiment the input force applied to the driven element 344 of the control mechanism is transmitted to a capstan 930. Capstan 930 is positioned within an elongated opening 934 of an input link 964. The opening 934 allows the input link 964 to slide linearly relative to the capstan 930. A cable 932 is coupled to the input link 964 and engages the capstan 930 so that rotational movement of the capstan 930 results in linear translation of the input link 964 in the W and I directions, depending on the direction of rotation. In other embodiments, the cable 932 may be omitted and the capstan 930 directly coupled to the input link 964 (e.g., rack and pinion or other gearing or a crank) to actuate linear movement of the input link 964.

The distal end of the input link 964 is rotatably coupled to a proximal end of a lever 960 at third pivot point 966. The distal end of the lever 960 is coupled to the drive element 954 by a collar 962. An intermediate portion of the lever 960 is rotatably coupled to a second pivot point 974 (fulcrum) on the support link 970.

It may be desirable to position the third pivot point 966 and the first pivot point 972 at equal distances from the second pivot point 974 so that pulling on input link 964 does not create a moment on the support link 970. When the second pivot point 974 is precisely midway between the third pivot point 966 and the collar 962, the force F on the drive element 954 equals that at third pivot point 966, so that 2F is applied at the second pivot point 974. When the second pivot point 974 is halfway between the housing 952 and the first pivot point 972, this 2F force is split evenly between the first pivot point 972 and the housing 952, so that F is applied equally and oppositely to the housing 952.

In other embodiments, the second pivot point 974 may be located at a point other than the midway point between the third pivot point 966 and the collar 962. If the third pivot point 966 and the first pivot point 972 are at equal distances from the second pivot point 974, then the forces at the third pivot point 966 and the collar 962 would no longer be equal, but they would be unequal in the same proportion as the forces at the first pivot point 972 and the housing 952. Thus, the drive element and drive element housing forces would still be opposite.

The rotational input force from 344 results in rotational movement of the capstan 930. This movement, in turn, causes the input link 964 to translate linearly. Upward movement of the third pivot point 966 causes the lever 960 rotate about the second pivot point 974, thereby causing the distal end of the lever 960 to apply a compressive force on the drive element 954. Similarly, downward movement of the third pivot point 966 causes the distal end of the lever 960 to apply a tensile force on the drive element 954.

The coupling of the lever 960 to the support link 970 causes the distal end of the support link 970 to apply a force to the housing 952 in the opposite direction as the force being applied to the driving element 954. The location of the second pivot point 974 along the length of the support link 970 determines the ratio of the input force to end effector actuation force. In this embodiment the second pivot point 974 is located exactly between the first pivot point 972 and the housing 952. In other embodiments, it may be desirable to relocate the second pivot point 974 so as to change the ratio. This may be desirable, for example, to enable a motor or solenoid driving the capstan 930 with a small force over an extended distance to close an end effector gripper requiring a large force over a short distance.

This embodiment may advantageously decouple the input force from joint movement of the driving element 954 and housing 952. This decoupling ensures that the input force effectively actuates relative movement between the driving element 954 and the housing 952, yet is not affected when the driving element 954 and housing 952 are jointly acted upon by external forces (such as, e.g., when the wrist assembly 320 is articulated). Thus, movement of the wrist assembly 320 will not affect grip position, and the grip movement and grip force will not affect the position of the wrist assembly 320. The movement of the joints can then be controlled more smoothly and accurately.

Figure 9B:
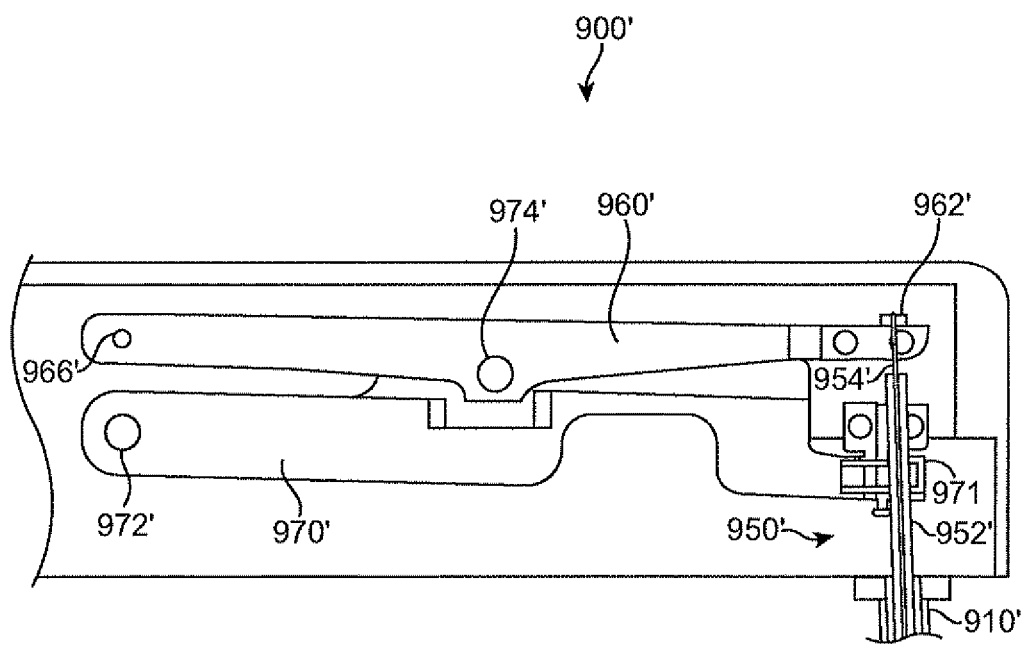

FIG. 9B is a cross-sectional view of a portion of a surgical instrument 900', similar to the surgical instrument 900 described above with respect to FIG. 9A, but including a radial ball bearing to support the housing 952' axially while enabling rotation of the housing 952'.

Drive Element and Drive Element Housing

The actuator assembly used to actuate movement of the end effector or other distal end component of the instrument may be provided in a variety of forms, depending on the application. In particular, the actuator assembly should be capable of operation regardless of the extent of articulation of intermediate joint regions. Therefore, the bend angle and bend radius of the intermediate joint regions should be one factor in selecting the drive element and drive element housing for the actuator assembly. In addition, if the instrument body rotates, the drive element and drive element housing must accommodate such rotation. In one exemplary embodiment the instrument body rotates approximately 270 degrees in either direction. The drive element's small diameter accommodates the twist from this rotation. The drive element housing, however, may be too stiff to accommodate the twist, and so one or more rotating joints as described above with reference to link 970 (FIG. 9) or below in FIG. 10 are used to accommodate the instrument body rotation.

In some embodiments, a conventional spring wind may be used for the drive element housing. However, bending of a spring wind housing may result in a change in overall length of the actuator assembly. This change may be undesirable if the intermediate joints are configured for significant range of motion.

In accordance with aspects of the invention, a drive element housing is provided that is capable of accommodating relative rotation of the proximal and distal ends of the housing, while being able to transmit compressive and tensile forces.

Figure 10:
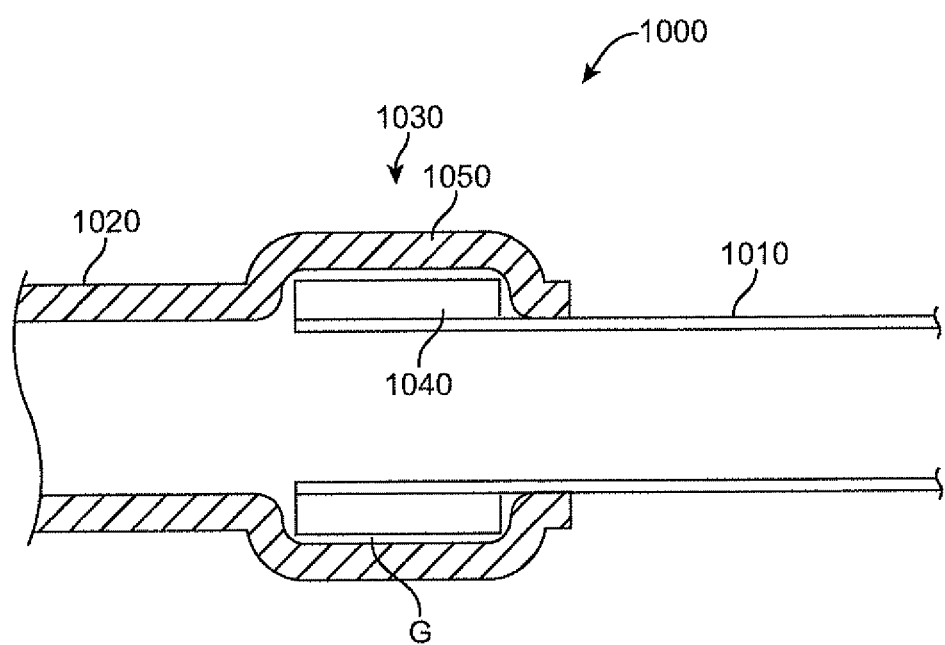
FIG. 10 is a cross-sectional view of a housing for carrying a drive element.

FIG. 10 shows one example of a drive element housing 1000 for carrying a drive element, such as a cable. The housing 1000 comprises a first cylindrical portion 1010 and a second cylindrical portion 1020, which are coupled at a coupling portion 1030. Coupling portion 1030 permits relative rotation between the first and second portions 1010,1020. In this embodiment, the coupling portion 1030 comprises a first enlarged portion 1040 of the first cylindrical portion 1010 received within a second enlarged portion 1050 of the second cylindrical portion 1020. A sufficient clearance gap G is provided between the second enlarged portion 1050 and the first enlarged portion 1040 so as to enable the first enlarged portion 1040 to rotate within the second enlarged portion 1050. However, the inner diameter of the second enlarged portion 1050 reduces on either side of the first enlarged portion 1040 so as to prevent significant relative movement in the direction of the longitudinal axis, between the first portion 1010 and the second portion 1020. In one embodiment, the first portion 1010 comprises a 0.027-inch ID×0.03-inch OD tube, the second portion 1020 comprises a 0.042-inch ID×0.058-inch OD tube. The first enlarged portion 1040 comprises an annular ring of 0.035-inch ID×0.042-inch OD.

Figure 11:
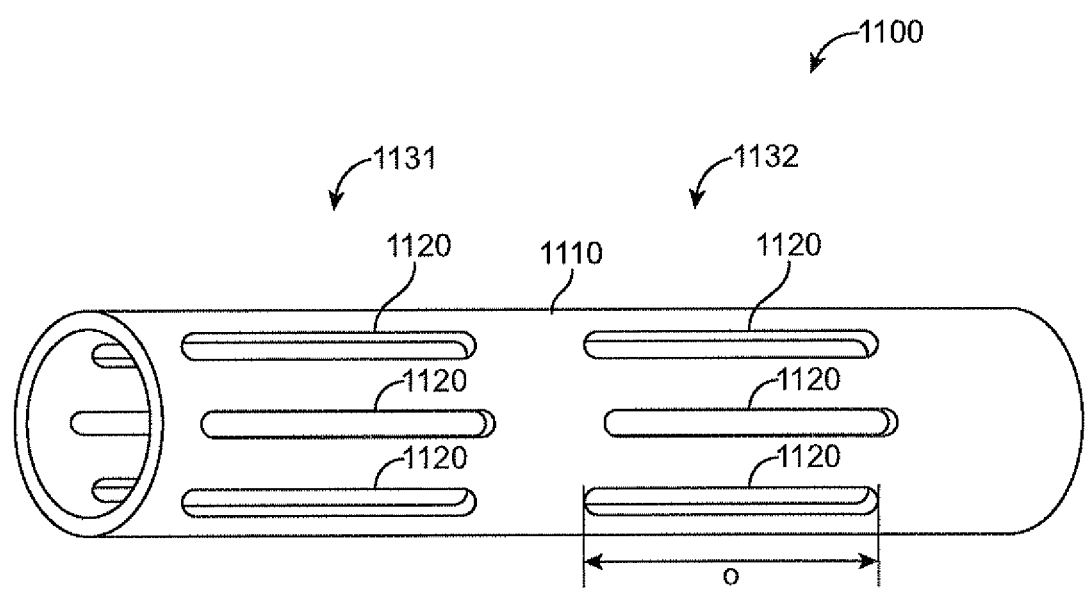
FIG. 11 is a perspective view of a housing for carrying a drive element.

FIG. 11 shows another example of a drive element housing 1100. In this embodiment, the housing 1100 comprises a hollow tube 1110 of 302 stainless steel having a plurality of longitudinal slits 1120. These slits 1120 are provided in one or more sets (e.g., sets 1131 and 1132), each set comprising a series of slits 1120 provided at various radial positions around the circumference of the tube 1110. These slits 1120 enable the tube 1110 to twist at the locations of the slits 1120 while maintaining axial stiffness so as to transmit tensile and compressive forces. In contrast with the embodiment shown in FIG. 10, this embodiment provides an alternate way to accommodate rotation of the housing 1100.

The size and location of the slits 1120 may be varied, depending on the application. For example, in some embodiments where the housing 1100 passes through a joint region capable of bending in multiple directions, the slits 1120 may be provided at equally spaced locations around the circumference of the housing 1100. The slits 1120 can be a few thousandths of an inch wide such that the metal remaining between the slits 1120 forms rods 0.008-inches wide and 0.15-inches long. The linear longitudinal slits 1120 shown in FIG. 11 may be used to accommodate twisting as the instrument rolls. In other embodiments, slits formed in a helical pattern may be provided in the housing to accommodate bending of the housing at the location of the slits. Any shortening of tube 1110 due to the twisting is negligible.

Figure 12A:
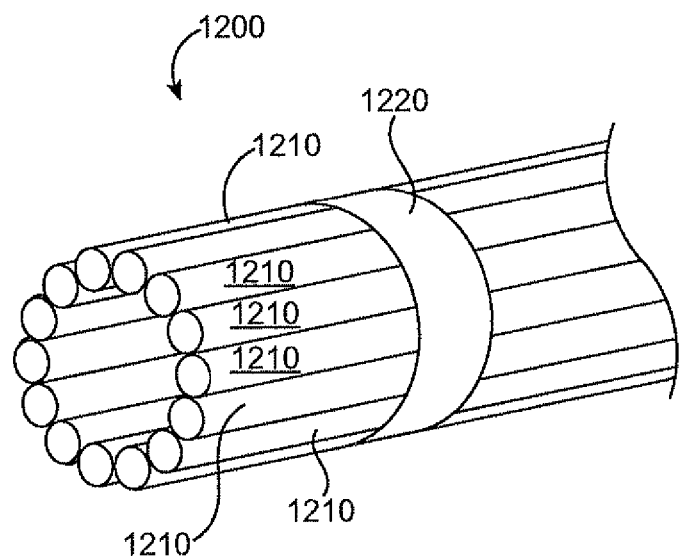
FIGS. 12A and 12B are perspective views of housings for carrying drive elements.

FIG. 12A shows yet another example of a drive element housing 1200. In this embodiment, the housing 1200 comprises a plurality of wires 1210 arranged to form a tube. For example, the housing 1200 may comprise twenty wires 1210, each having a diameter of 0.008-inches. These wires 1210 may be coupled together at multiple coupling regions 1220 along the length of the housing 1200. These coupling regions 1220 may comprise, e.g., weld points where the wires 1210 are welded together. This structure may provide good stiffness in tension and compression while permitting some torsion, which can be adjustable based on selection of the wires 1210 and the spacing of the coupling regions 1220. The wires 1210 may comprise, e.g., 302 stainless steel or a nickel-titanium (NiTi) alloy (e.g., Nitinol). Nitinol may be desirable for its "superelastic" behavior, enabling the material to maintain its shape even after a 2-percent or even 8-percent strain.

In another embodiment, each coupling region 1220 comprises a solid metal cylinder having longitudinal holes formed in the wall of the cylinder to enable the wires 1210 to pass through. Plastic spacers inside the diameter of the wires keep the spacers from sliding along the wires.

Figure 12B:
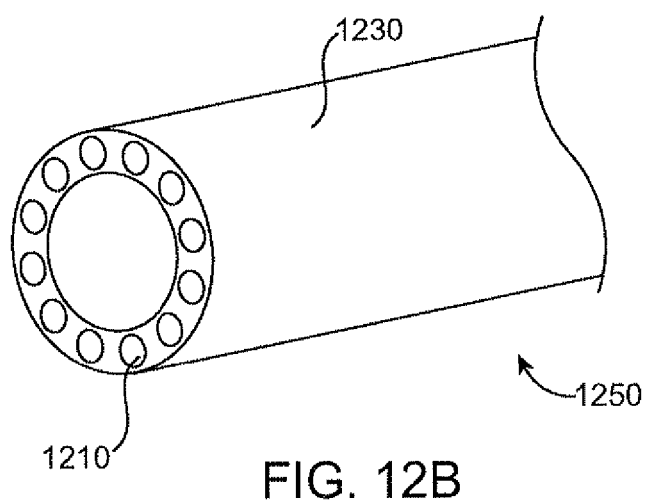

FIG. 12B shows another drive element housing 1250 that includes a plurality of wires 1210. In this embodiment a flexible coupling material 1230, such as a polymer, is extruded over the wires 1210. The flexible coupling material 1230 is used to prevent buckling of the wires 1210 when the housing 1250 is under a compressive axial load.

Figure 13:
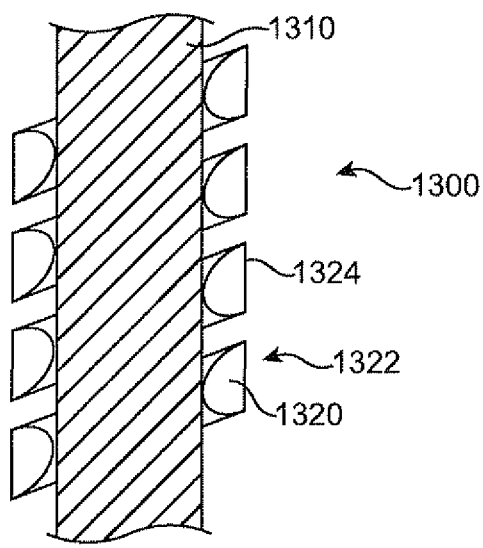
FIG. 13 is a cross-sectional view of a drive element for transmitting both compressive and tensile forces.

FIG. 13 shows an illustrative embodiment of a drive element 1300 that may be used to transmit both compressive and tensile forces to the end effector. As shown in FIG. 13, drive element 1300 comprises a central core 1310, which provides tensile strength, such as 0.018-inch diameter tungsten cable. In addition, the drive element 1300 comprises an outer layer 1320, which contains the tungsten core 1310 and provides the drive element 1300 with the ability to transmit compressive forces. In this embodiment, the outer layer 1320 comprises a second cable 1322 wrapped around the core 1310 in a spring-wind fashion. In some embodiments, the outer surface of the outer cable 1322 is ground down to form a flat surface 1324 to minimize friction and snagging with the interior of the drive element housing that carries the drive element 1300. These designs are similar to how the housings are sometimes produced for bicycle brake (flat wound rectangular wire) and shift (substantially parallel wires with a polymer liner) mechanisms.

Figure 14A:
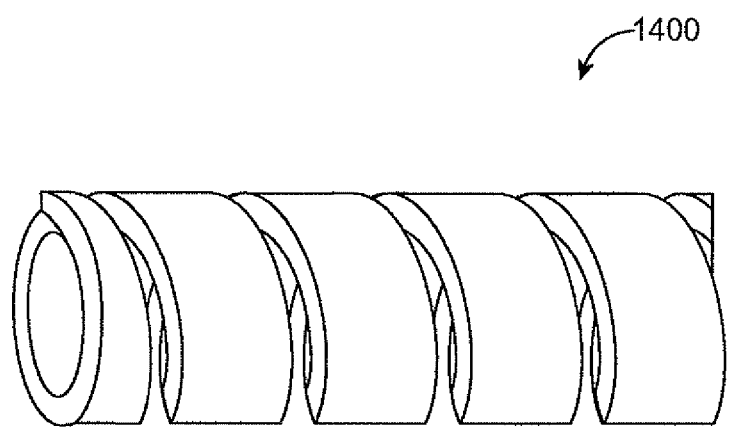
FIG. 14A is a perspective view of a housing for carrying a drive element.
Figure 14B:
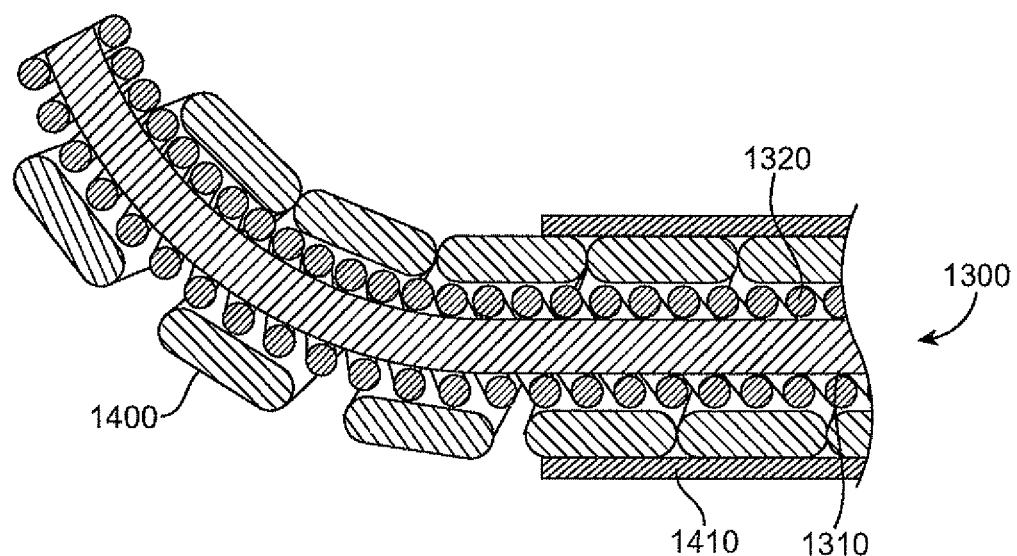
FIG. 14B is a cross-sectional view of a housing and a drive element.

FIGS. 14A and 14B illustrate yet another drive element housing 1400 that may be used to carry the drive element 1300. This housing 1400 is formed from a ribbon-shaped wire having a rectangular cross-section, as can be seen in FIG. 14B, and wound in a helix, as can be seen in FIG. 14A. The spring-wind structure of the housing 1400 enables the housing 1400 to bend at the intermediate joint regions, and the rectangular cross-section enables the housing 1400 to better transmit tensile forces than a round wire spring-wind housing. A plastic sheath 1410 may be provided over the ribbon-shaped wire so as to reduce friction between the housing 1400 and the passages through which the housing 1400 passes.

Figure 15:
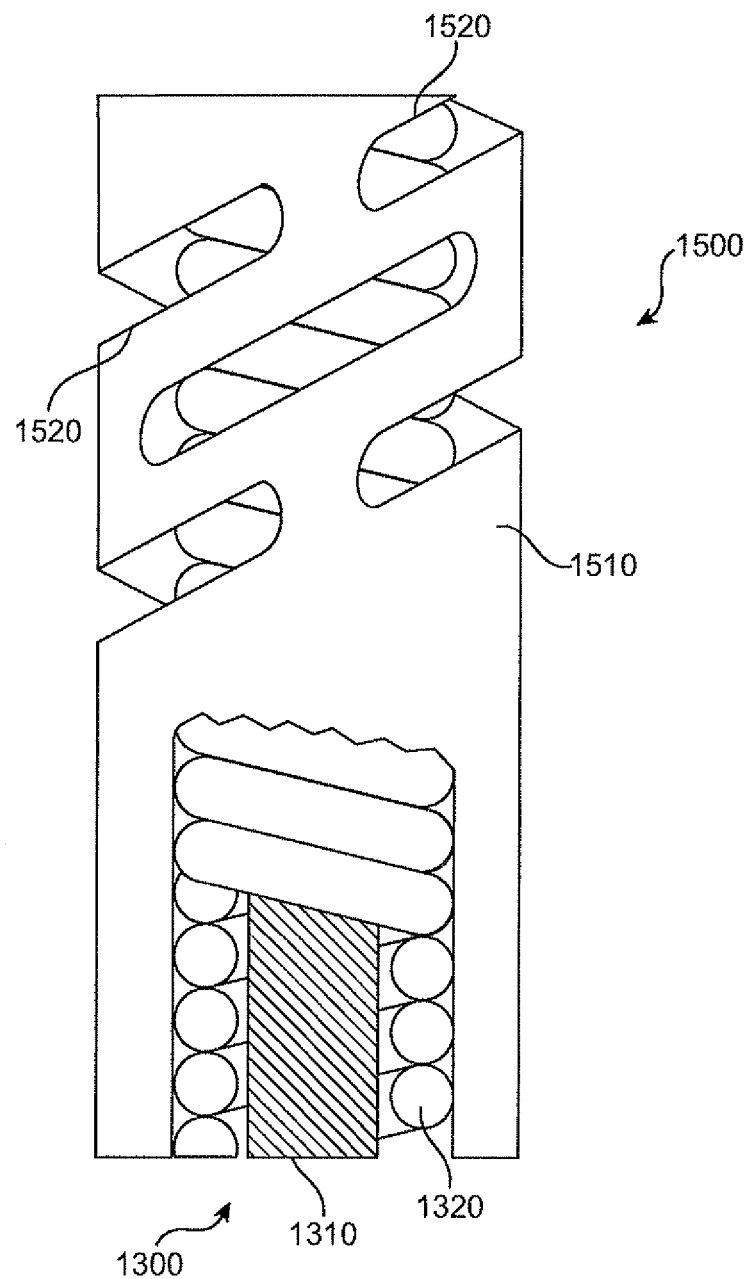
FIG. 15 is a cross-sectional view of another housing and a drive element.

FIG. 15 depicts another illustrative drive element housing 1500 that may be used to carry the drive element 1300. In the depicted embodiment, the drive element housing 1500 is a Nitinol tube 1510 having a plurality of slits 1520 formed only in the regions of the housing 1500 that correspond to the intermediate joint regions through which housing 1500 passes. Unlike the slits 1120 shown in FIG. 11, these slits 1520 are formed at an angle to the longitudinal axis of the housing 1500 (i.e., angled kerf cuts that penetrate to the tube's hollow center) and in a direction different from the winding of the cable 1322. This opposite angling can prevent the spring wind cable 1322 from snagging on the slits 1520 while providing the housing 1500 with flexibility for bending in the joint regions of the instrument.

Figure 16B:
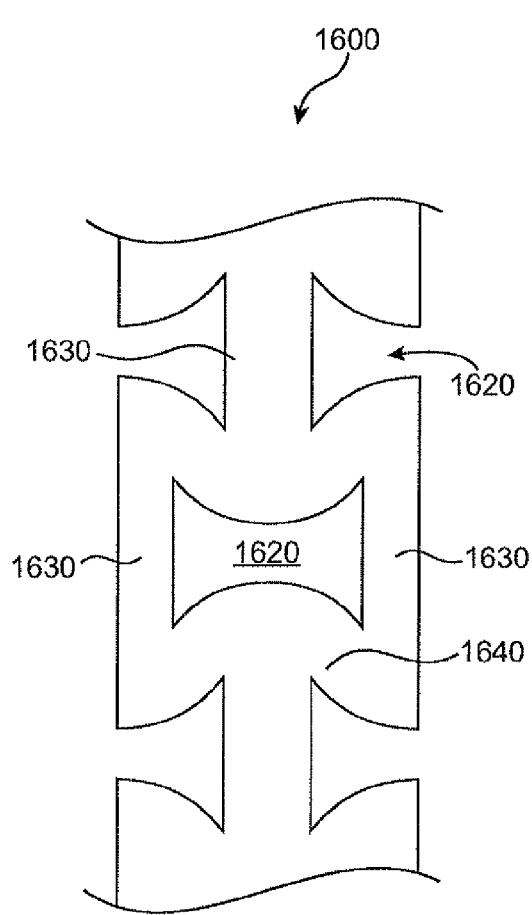
FIG. 16A shows a perspective view, and FIG. 16B show a plan view, of a housing.
Figure 16A:
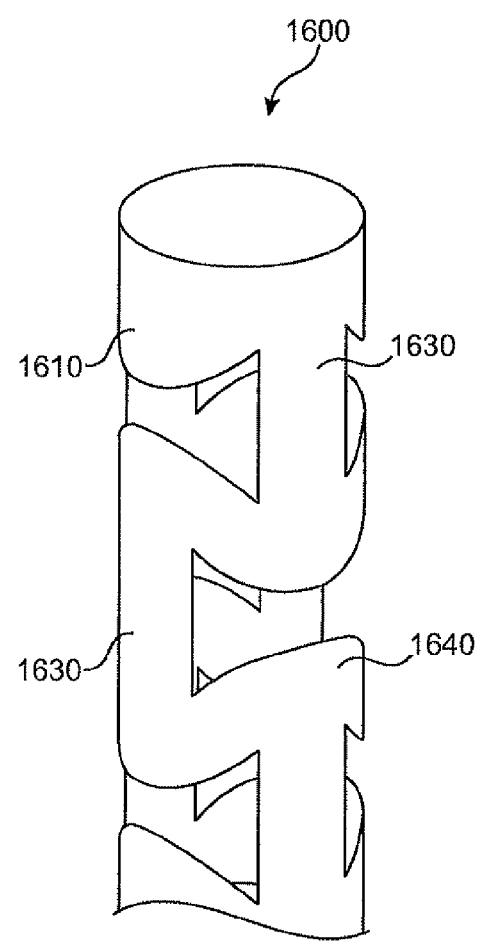

FIG. 16A shows a perspective view, and FIG. 16B shows a plan view, of still another illustrative drive element housing 1600. In this embodiment, the housing 1600 is a solid nitinol tube 1610 having a plurality of shaped apertures 1620 formed in the walls of the tube 1610 (e.g., dovetail-shaped kerf cuts that penetrate to the tube's hollow center, as shown). This drive element housing 1600 configuration provides good tensile strength and enables housing 1600 to be bent in a tight radius.

In this embodiment, the apertures 1620 form longitudinal portions 1630 and connecting portions 1640 in the tube 1610. The longitudinal portions 1630 provide axial stiffness to the housing 1600 and are provided at locations offset by 90 degrees around the circumference of the tube 1610. This enables the housing 1600 to bend at the locations of the apertures 1620 in any direction.

For example, if a Nitinol tube having a outer diameter of 0.63-inches and an inner diameter of 0.043-inches is used as the tube 1610, and approximately 50 percent of the material is removed to form the apertures 1620, the overall strength of the tube 1610 can approximate that of a 0.018" tungsten cable.

Distal Portion of the Surgical Instrument

Figure 17:
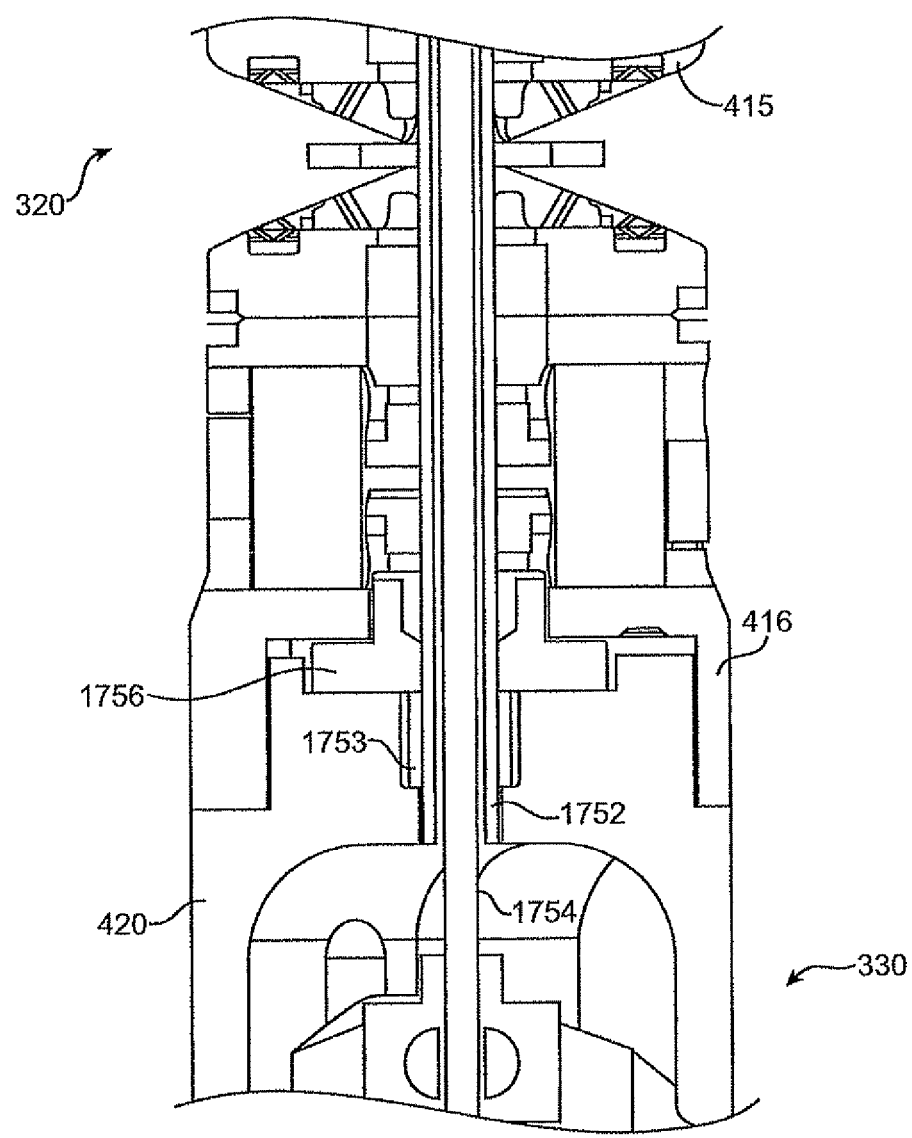
FIG. 17 is a cross-sectional view of a portion of a surgical instrument.

FIG. 17 is a cross sectional view of a distal portion of a surgical instrument that illustrates how the drive element and drive element housing are positioned at the region where the wrist assembly 320 is coupled to the end effector 320. Distal link 416 is coupled to gripper clevis 420 as shown. Drive element housing 1752 extends through wrist assembly 320 and is braced against end effector 330's gripper clevis 420. Drive element 1754 extends through drive element housing 1752 and is coupled to operate end effector 330's jaws. An annular collar 1753 is coupled to the distal end of drive element housing 1752. In one instance annular collar 1753 is a segment of Nitinol tubing (0.031-inch ID×0.041-inch OD) welded over drive element housing 1752. In addition, flange 1756 is positioned between the gripper clevis 420 and the distal link 416. The collar 1753 is positioned between the flange 1756 and the gripper clevis 420 to prevent motion of drive element housing 1752 along the longitudinal axis. When a tensile force is applied to drive element housing 1752 at the control mechanism 340, the collar 1753 applies that tensile force to flange 1756. In turn, flange 1756 applies the force to the distal link 416 of wrist assembly 320. When a compressive force is applied to the housing 1752, the collar 1753 applies the compressive force to the gripper clevis 420. As described above, these forces help counteract forces being applied by drive element 1754.

Figure 18A:
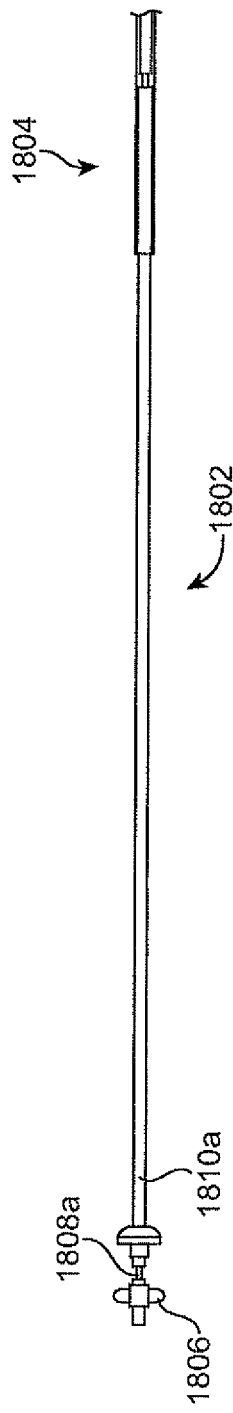
FIG. 18A is a cross-sectional view of an illustrative drive element and drive element housing.
Figure 18B:
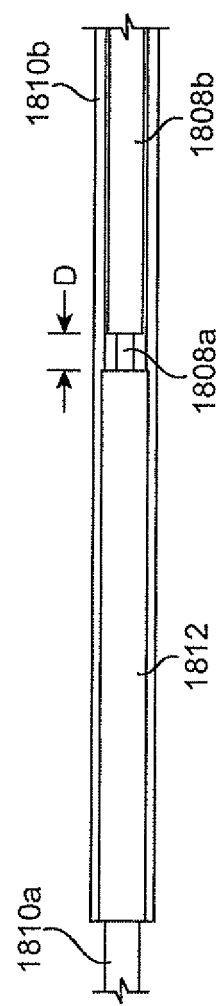
FIG. 18B is a cross-sectional view of a detail of FIG. 15A.

FIG. 18A is a partial cross-sectional view of an illustrative drive element and drive element housing combination, and FIG. 18B is a cross-sectional view of a detail of FIG. 18A. As shown in FIG. 18A, the combination includes two sections. The combination's first section 1802 is the distal section. This distal section 1802 runs through wrist assembly 320 in instrument 120s distal portion 350. The combination's proximal section 1804 (only a portion is shown) runs through the substantially rigid portion of the instrument body as described above. And as described above, both the distal and proximal sections 1802, 1804 have a drive element and drive element housing.

In distal section 1802, cross pin member 1806 attaches to the movable part or parts (e.g., gripper jaws) of the end effector. Distal drive element portion 1808a is coupled to cross pin member 1806 and extends through distal drive element housing portion 1810a. In one exemplary embodiment, distal drive element portion 1808a is a 0.016-inch Nitinol wire (not heat treated, but 40 percent cold worked). Distal drive element housing portion 1810a is a 0.020-inch ID×0.030-inch OD Nitinol tube. Since the Nitinol tube's diameter is small, it accommodates the wrist bending.

In proximal section 1804, proximal drive element portion 1808b extends through proximal drive element housing portion 1810b. In this exemplary embodiment, proximal drive element portion 1808*b* is a 0.017-inch ID×0.035-inch OD 302 stainless steel hypotube. Due to the difficulty in purchasing 0.017-inch ID×0.035-inch OD 302 stainless steel hypotubes, the proximal drive element portion 1808*b* may be formed by fitting a 0.017-inch ID×0.025-inch OD hypotube inside of a 0.0275-inch ID×0.0355-inch OD hypotube. Proximal drive element housing portion 1810*a* is a rigid 0.042-inch ID×0.058-inch OD 302 stainless steel hypotube. Stainless steel rather than Nitinol hypotubes are used due to decreased cost and increased stiffness.

Distal and proximal drive elements 1808*a*,1808*b* are joined by, e.g., crimping. Since the outer diameter of distal drive element housing portion 1810*a* is smaller than the inner diameter of proximal drive element housing portion 1810*b*, a stainless steel tube 1812 is inserted between the drive element housing portions 1810*a*,1810*b* and is secured by, e.g., crimping or welding. To allow for drive element movement, the distal end of proximal drive element portion 1808*b* is set back a distance D from the proximal end of tube 1812. The distance D is made large enough to allow for full actuation but small enough to prevent distal drive element portion 1808*a* from buckling under compression before entering distal drive element housing 1810*a*.

Embodiments of the present invention may provide various advantages not provided by prior art systems. For example, embodiments may enable a surgical instrument to provide balanced force actuation to a distal articulating mechanism through a joint region capable of a large range of motion.

While the invention has been described in terms of particular embodiments and illustrative figures, those of ordinary skill in the art will recognize that the invention is not limited to the embodiments or figures described. For example, in the embodiments described above, the drive elements pass through a first joint region (e.g., the wrist assembly) to manipulate the end effector. In other embodiments, the drive elements which pass through the first joint region may be used to manipulate other articulating mechanisms, such as additional joints or wrist assemblies.

Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

We claim:

1. A surgical instrument, comprising:
a control mechanism comprising a driven element and a mechanism, the driven element being configured to receive an actuating force;
an instrument body comprising a proximal portion, a distal portion, and a joint, the joint being positioned between the proximal and distal portions of the instrument body, wherein the proximal portion of the instrument body is coupled to the control mechanism;
a component coupled to a distal end of the instrument body;
a drive element housing comprising a proximal portion and a distal portion, the distal portion of the drive element housing being coupled to the component, and the proximal portion of the drive element housing being coupled to the mechanism, wherein the drive element housing extends through the proximal portion of the instrument body, through the joint, and through the distal portion of the instrument body to the component; and
a drive element coupled to the driven element to receive the actuating force from the driven element, the drive element being coupled to the component to transfer the actuating force to the component, the drive element extending between the component and the driven element, and the drive element extending through the drive element housing;
wherein the actuating force actuates the component;
wherein, in response to the actuating force on the drive element, the mechanism applies a second force to the proximal portion of the drive element housing, the second force being in a direction opposite to a direction of the actuating force; and
wherein the drive element housing transfers the second force to the component.

2. The surgical instrument of claim 1:
wherein the drive element comprises a first section that extends through an essentially rigid portion of the instrument body and a second section that extends through the joint;
wherein the first section comprises an essentially rigid hypotube; and
wherein the second section comprises a filar.

3. The surgical instrument of claim 1, wherein the mechanism comprises an idler pulley coupled to the proximal portion of the drive element housing and coupled to the drive element, wherein the idler pulley applies a compressive force to the proximal portion of the drive element housing as the second force that the drive element housing transfers to the component.

4. The surgical instrument of claim 1, wherein the mechanism comprises a lever coupled to the proximal portion of the drive element housing and coupled to the drive element, wherein the lever applies a compressive or a tensile force to the drive element housing as the second force that the drive element housing transfers to the component.

5. The surgical instrument of claim 1, wherein the mechanism comprises:
a lever coupled to the drive element, wherein the lever transmits a force to the drive element; and
a linkage coupled to the drive element housing and to the lever,
wherein the drive element housing is coupled to the linkage to rotate with reference to the linkage, and
wherein the linkage transmits the second force to the proximal portion of the drive element housing.

6. The surgical instrument of claim 1, wherein the mechanism comprises an anchor connected to the proximal portion of the drive element housing and connected to a chassis of the control mechanism, wherein a magnitude of the actuating force is approximately equal to a magnitude of the second force applied by the anchor.

7. The surgical instrument of claim 1, wherein the component comprises an end effector.

8. The surgical instrument of claim 1, wherein the component comprises an end effector that includes jaws, and the drive element actuates at least one of the jaws.

9. The surgical instrument of claim 1, wherein the drive element comprises a filar that applies a tensile force to the component.

10. The surgical instrument of claim 1, wherein the drive element comprises a filar that applies a compressive force to the component.

11. The surgical instrument of claim 10, wherein the filar comprises a cable.

12. The surgical instrument of claim 1, wherein the drive element comprises a helical winding.

13. The surgical instrument of claim 1:
wherein the drive element comprises a filar and a spring winding around the filar; and
wherein the filar provides a tensile force on the component and the spring winding provides a compressive force on the component.

14. The surgical instrument of claim 1, wherein the drive element housing comprises a tube; and wherein the drive element extends within the tube.

15. The surgical instrument of claim 14, wherein a plurality of slots are defined in the wall of the tube.

16. The surgical instrument of claim 14, wherein the tube is a solid piece that resiliently bends within the joint.

17. The surgical instrument of claim 1:
wherein the joint comprises a wrist assembly.

18. A method of operating a surgical instrument, the method comprising:
receiving an actuating force from a first driven element of a control mechanism at a drive element;
transferring, by the drive element, the actuating force to a component at a distal end of an instrument body, wherein the drive element extends through a drive element housing, wherein the drive element housing extends through a proximal portion of the instrument body, through a distal portion of the instrument body, and through a joint between the proximal and distal portions of the instrument body, and wherein the actuating force actuates the component;
applying, by a mechanism in the control mechanism in response to the actuating force on the drive element, a second force to a proximal portion of a drive element housing, the second force being in a direction opposite to a direction of the actuating force, and
transferring, by the drive element housing, the second force to the component.

19. The method of claim 18 further comprising:
moving the joint in response to a drive force from a second driven element of the control mechanism; and
keeping the actuating and second forces acting on the component essentially unchanged as the joint moves.

20. The method of claim 18, wherein the applying, by the drive element, the actuating force to the component comprises applying, by the drive element, the actuating force to an end effector.

21. The method of claim 18, wherein the transferring, by the drive element housing, the second force to the component comprises transferring, by the drive element housing, a force of approximately equal magnitude to the actuating force to the component.

22. The method of claim 18, wherein the drive element comprises a filar, and wherein the transferring the actuating force comprises transferring a tensile force on the filar.

23. The method of claim 18, wherein the drive element comprises a filar, and wherein the transferring the actuating force comprises transferring a compressive force on the filar.

* * * * *